US007871790B2

(12) United States Patent
Frucht et al.

(10) Patent No.: US 7,871,790 B2
(45) Date of Patent: Jan. 18, 2011

(54) ANTHRAX BIOASSAYS AND METHODS OF TREATING AND DIAGNOSING ANTHRAX INFECTION

(75) Inventors: David M. Frucht, Vienna, VA (US); Ruth Cordoba-Rodriguez, Baltimore, MD (US)

(73) Assignee: The United States of America as represented by the Department of Health and Human Services, Washington, DC (US)

( * ) Notice: Subject to any disclaimer, the term of this patent is extended or adjusted under 35 U.S.C. 154(b) by 655 days.

(21) Appl. No.: 11/071,799

(22) Filed: Mar. 2, 2005

(65) Prior Publication Data

US 2006/0246532 A1 Nov. 2, 2006

Related U.S. Application Data

(60) Provisional application No. 60/549,572, filed on Mar. 2, 2004.

(51) Int. Cl.

| | |
|---|---|
| *G01N 33/542* | (2006.01) |
| *G01N 33/60* | (2006.01) |
| *C12Q 1/37* | (2006.01) |
| *C12Q 1/18* | (2006.01) |
| *C12N 9/00* | (2006.01) |
| *C12N 9/54* | (2006.01) |

(52) U.S. Cl. .......................... 435/32; 435/23; 435/7.95; 435/183; 435/221

(58) Field of Classification Search ................ 435/7.95, 435/23, 32, 183, 221

See application file for complete search history.

(56) References Cited

PUBLICATIONS

Humke et al. 2000, Iceberg A Novel Inhibitor of Interleukin-1 Generation. Cell, vol. 103, pp. 99-111.*

Hanna et al 1993. On the role of macrophages in anthrax, Proceedings of the National Academy of Sciences, vol. 90, pp. 10198-102010.*

Okamoto et al 1999. Peptide Based Interleukin-Iβ Converting Enzyme (ICE) Inhibitors: Synthesis, Structure Activity Relationships and Crystallographic Study of the -ICE-inhibitor Complex. Chem. Pharm. Bulletin, vol. 47, No. 1, pp. 11-21).*

Ruth Cordoba-Rodriguez, et al. 2004. Anthrax Lethal Toxin Rapidly Activates Caspase-1/ICE and Induces Extracellular Release of Interleukin (IL)-1β and IL-18. The Journal of Biological Chemistry, vol. 79, No. 20, Issue of May 14, pp. 20563-20566.*

Chopra et al., "Anthrax Lethal Factor Proteolysis and Inactivation of MAPK Kinase," *J. Biol. Chem.* 278:9402-9406 (2003).

Erwin et al., "Macrophage-Derived Cell Lines Do Not Express Proinflammatory Cytokines after Exposure to *Bacillus anthracis* Lethal Toxin," *Infect. Immun.* 69:1175-1177 (2001).

Fellows et al., "Efficacy of a Human Anthrax Vaccine in Guinea Pigs, Rabbits, and Rhesus Macaques Against Challenge by *Bacillus anthracis* Isolates of Diverse Geographical Origin," *Vaccine* 19:3241-3247 (2001).

Fritz et al., "Pathology of Experimental Inhalation Anthrax in the Rhesus Monkey," *Lab. Invest.* 73:691-702 (1995).

Hanna et al., "On the Role of Macrophages in Anthrax," *Proc. Natl. Acad. Sci. USA* 90:10198-10201 (1993).

Ivins et al., "Comparative Efficacy of Experimental Anthrax Vaccine Candidates Against Inhalation Anthrax in Rhesus Macaques," *Vaccine* 16:1141-1148 (1998).

Maynard et al., "Protection Against Anthrax Toxin by Recombinant Antibody Fragments Correlates with Antigen Affinity," *Nature Biotechnol.* 20:597-601 (2002).

Meyerhoff et al., "US Food and Drug Administration Approval of Ciprofloxacin Hydrochloride for Management of Postexposure Inhalational Anthrax," *CID* 39:303-308 (2004).

Moayeri et al., "*Bacillus anthracis* Lethal Toxin Induces TNF-α-Independent Hypoxia-Mediated Toxicity in Mice," *J. Clin. Invest.* 112:670-682 (2003).

Pickering et al., "Cytokine Response to Infection with *Bacillus anthracis* Spores," *Infect. Immun.* 72:6382-6389 (2004).

Popov et al., "Effect of *Bacillus anthracis* Lethal Toxin on Human Peripheral Blood Mononuclear Cells," *FEBS Lett.* 527:211-215 (2002).

Vasconcelos et al., "Pathology of Inhalation Anthrax in Cynomolgus Monkeys (*Macaca fascicularis*)," *Lab. Invest.* 83:1201-1209 (2003).

Zaucha et al., "The Pathology of Experimental Anthrax in Rabbits Exposed by Inhalation and Subcutaneous Inoculation," *Arch. Pathol. Lab. Med.* 122:982-992 (1998).

Agrawal and Pulendran, "Anthrax lethal toxin: a weapon of multisystem destruction," *Cell. Mol. Life Sci.* 61:2859-2865, 2004.

Ascenzi et al., "Anthrax toxin: a tripartite lethal combination," *FEBS Letters* 531:384-388, 2002.

Erwin et al., "Macrophage-Derived Cell Lines Do Not Express Proinflammatory Cytokines after Exposure to *Bacillus anthracis* Lethal Toxin," *Infection and Immunity* 69(2): 1175-1177, 2001.

Moayeri et al., "*Bacillus anthracis* lethal toxin induces TNF-α-independent hypoxia-mediated toxicity in mice," *J. Clin. Invest.* 112(5):670-682, 2003.

Moayeri and Leppla, "The roles of anthrax toxin in pathogenesis," *Current Opinion in Microbiology* 7:19-24, 2004.

* cited by examiner

*Primary Examiner*—Jon P Weber
*Assistant Examiner*—Kailash C Srivastava
(74) *Attorney, Agent, or Firm*—Klarquist Sparkman, LLP

(57) ABSTRACT

Based on the observation that exposure of cells or animals to anthrax lethal toxin results in activation of the intracellular enzyme caspase-1/IL-1 converting enzyme (ICE), which, in turn, leads to production and extracellular release of the cytokine substrates of ICE: interleukin 1 beta (IL-1β) and interleukin 18 (IL-18), disclosed herein are bioassays that can be used to determine the efficacy of a potential anthrax therapeutic agent and for screening test agents to identify anthrax therapeutic agents. Also disclosed herein are methods of diagnosing and treating anthrax infection.

6 Claims, 7 Drawing Sheets

ANTHRAX BIOASSAYS AND METHODS OF TREATING AND DIAGNOSING ANTHRAX INFECTION

CROSS-REFERENCE TO RELATED APPLICATION

This application claims priority to U.S. Provisional Application No. 60/549,572 filed Mar. 2, 2004, herein incorporated by reference in its entirety.

FIELD

This application relates to methods of determining the efficacy of an anti-anthrax therapeutic, as well as methods of diagnosing and treating anthrax infections.

BACKGROUND

Patients with anthrax infection recognized at late stages have high mortality even with appropriate antibiotic therapy (*MMWR Morb. Mortal Wkly. Rep.* 50:1049-51, 2001), which is likely due to the effects of bacterial toxins that persist following death of the pathogen. One of these toxins, anthrax lethal toxin (LT), includes three distinct components: anthrax protective antigen (PA), anthrax edema factor (EF), and anthrax lethal factor (LF). Anthrax PA binds target cells and allows entry of the enzymatically active anthrax LF (Lacy and Collier, *Curr. Top. Microbiol. Immunol.* 271:61-85, 2002). LF, in turn, inactivates mitogen activated protein kinase kinases (MAPKKs) through cleavage at specific recognition sites (Moayeri et al. *J. Clin. Invest.* 112:670-82, 2003; Duesbery et al., *Science* 280:734-7, 1998; Vitale et al., *Biochem. Biophys. Res. Commun.* 248:706-11, 1998; Pellizzari et al. *FEBS Lett.* 462:199-204, 1999; and Park et al., *Science* 297: 2048-51, 2002). MAPKKs are intermediates in signal transduction cascades that ultimately lead to activation of the NF-κB family of transcription factors that promote macrophage survival (Park et al., *Science* 297:2048-51, 2002).

Although some of the elements underlying the mechanism of action of anthrax LT-induced apoptosis have been determined, the etiology of species- and cell-specific differences in sensitivity to anthrax LT remains unclear. In addition, the role of other downstream effectors, such as cytokines, is disputed. In this regard, seemingly contradictory reports have been published that either support or reject roles for pro-inflammatory cytokines in responses to anthrax LT in vitro (Hanna et al. *Proc. Natl. Acad. Sci. USA* 90:10198-201, 1993; Erwin et al., *Infect. Immun.* 69:1175-7, 2001). Therefore, a clearer understanding of downstream effectors is needed. Such an understanding will permit identification of agents that can be used to treat or diagnose an anthrax infection, as well as methods of treating or diagnosing an anthrax infection.

SUMMARY

It is disclosed herein that anthrax lethal toxin (LT) activates the intracellular enzyme Caspase-1/IL-1 Converting Enzyme (ICE), which, in turn, leads to activation and extracellular release of the cytokine substrates of ICE: interleukin 1 beta (IL-1β) and interleukin 18 (IL-18). This activation of ICE and release of the ICE-dependent cytokines IL-1β and IL-18 is demonstrated both in vitro and in vivo. Extracellular accumulation of IL-1β and IL-18 was observed within 24 hours of anthrax LT treatment. Induction of IL-1β and IL-18 by anthrax LT was found to be ICE-dependent, as it is blocked by small molecule inhibitors of ICE such as Z-WEHD-FMK.

Based on the observation that ICE, IL-1β, and IL-18 are biologically relevant downstream effectors of anthrax LT, novel bioassays for anthrax biological activity and therapeutic targets are disclosed. In particular examples, the disclosed methods more closely correlate with toxin-induced pathology than previous methods, because it more closely reflects the biological action of anthrax LT in vivo.

Methods are disclosed for determining the efficacy of a potential anti-anthrax therapeutic, or identifying an agent that decreases the pathogenicity of anthrax, such as an agent that targets anthrax LT. In particular examples, the method includes contacting one or more test agents with a cell expressing ICE, such as at least one, at least two, at least three, or at least four test agents, and determining whether ICE activity is decreased in the cell, wherein a decrease in ICE activity indicates the test agent decreases pathogenicity of anthrax (for example by interfering with the biological activity of *B. anthracis* spores or anthrax LT). In particular examples, the cell expressing ICE is infected with anthrax, for example by contacting the cell with anthrax toxin (such as anthrax LT) or *B. anthracis* spores which induce activation of ICE.

In one example, ICE activity is determined by measuring the activity of activated ICE, for example by measuring the activity of an ICE-dependent cytokine, such as the activity of activated IL-1β or activated IL-18. In particular examples, ICE activity is determined by measuring an amount of activated ICE or ICE-dependent cytokine present. For example, an amount of intracellular activated ICE, or an amount of extracellular activated IL-1β or activated IL-18 protein, can be determined.

In particular examples, the method further includes comparing the observed ICE activity in the presence of the test agent to ICE activity in the absence of the test agent, for example by comparing ICE activity to a baseline. In some examples, the observed ICE activity is compared to ICE activity in the presence of a control, such as a positive or negative control. An example of a positive control is a cell (or a sample from such a cell) exposed to an agent known to decrease anthrax pathogenicity (such as ciprofloxacin hydrochloride or a neutralizing antibody to anthrax LT), wherein similar ICE activity relative to the positive control indicates the test agent decreases pathogenicity of anthrax. An example of a negative control is a cell (or a sample obtained from such a cell) infected with anthrax and an agent known to not affect anthrax pathogenicity, wherein decreased ICE activity relative to the negative control indicates the test agent decreases pathogenicity of anthrax.

The disclosed methods can be conducted in vitro (such as in a cell culture), or in vivo (such as in a laboratory animal). For example, an agent observed in vitro to have a therapeutic effect on anthrax infection can be subsequently screened in vivo to further assess the efficacy of the potential anti-anthrax agent. In one example, the cells used are macrophages, such as the RAW264.7 and J774A.1 cell lines. Exemplary laboratory animals include non-human primates (such as cynomolgus monkeys and rhesus macaques), as well as rodents (such as mice, rats, rabbits and guinea pigs).

Also provided by the present disclosure are methods of diagnosing an anthrax infection in a subject, such as infection with *B. anthracis* or a spore thereof, or exposure to anthrax LT. In particular examples, the method includes determining whether ICE activity is increased in a sample obtained from the subject, wherein an increase in ICE activity indicates the subject is infected with anthrax. In one example, ICE activity is determined by measuring the activity of activated ICE, for example by measuring the activity of an activated ICE-dependent cytokine, such as the activity of activated IL-1β or activated IL-18. In a particular example, ICE activity is determined by measuring an amount of activated ICE or ICE-dependent cytokine present. For example, an amount of intracellular activated ICE, or an amount of extracellular activated IL-1β or activated IL-18 protein, can be determined.

In particular examples, the method further includes comparing the observed ICE activity in the subject to ICE activity observed in the absence of anthrax infection, or to ICE activity observed in the presence of anthrax infection. If the observed ICE activity in the subject is similar to the ICE activity observed in the absence of anthrax infection, this indicates the subject does not have an anthrax infection. In contrast, if the observed ICE activity in the subject is similar to the ICE activity observed in the presence of anthrax infection, this indicates the subject has been exposed to anthrax LT, either through exogenous administration of active anthrax infection.

Methods for treating infection by anthrax are also disclosed. In particular examples the method includes decreasing ICE activity in the subject, for example by administration of a therapeutically effective amount of an agent that reduces the biological activity of ICE, for example by decreasing the activity of an ICE-dependent cytokine (such as IL-1β or IL-18). For example, ICE activity can be decreased by reducing an amount of activated ICE or ICE-dependent cytokine present, for example by reducing the mRNA or protein levels of ICE or an ICE-dependent cytokine (such as activated L-1β or IL-18) in the cell. In particular examples, such methods reduce systemic shock during anthrax infection. Illustrative examples of ICE inhibitors include Z-WEHD-FMK (including analogs thereof), and the inhibitors disclosed in US 2003/0224403-A1, U.S. Pat. No. 6,335,618 and U.S. Pat. No. 6,136,787, all of which examples of inhibitors are incorporated herein by reference.

The foregoing and other objects, features, and advantages of the disclosure will become more apparent from the following detailed description, which proceeds with reference to the accompanying figures.

DETAILED DESCRIPTION

Abbreviations and Terms

Figure 1B:
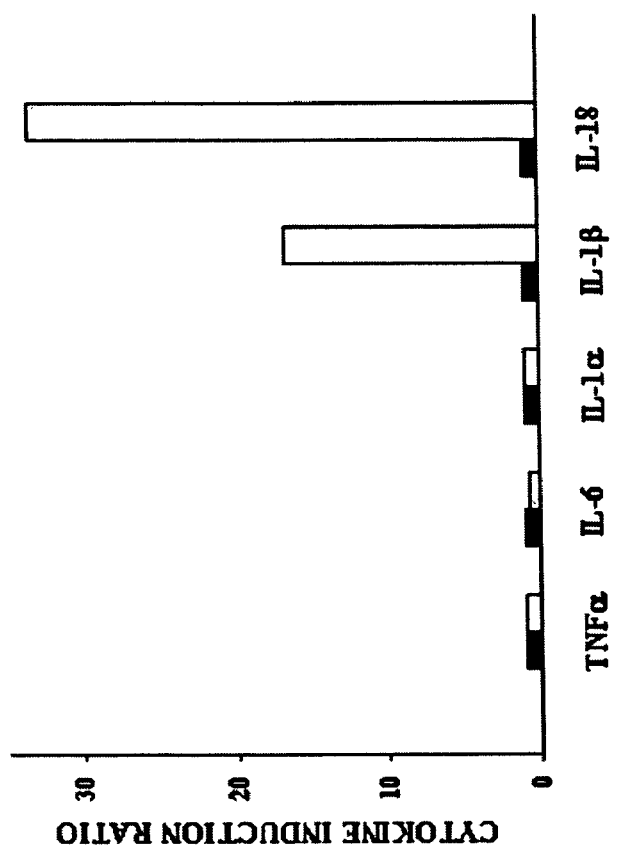
FIGS. 1A and 1B are bar graphs showing cytokine induction by LT in RAW264.7 (A) and J774A.1 (B) cells. The y-axis values represent the ratio of induction of the various cytokines (gray bars) compared to unstimulated cells (black bars, arbitrarily assigned a value of 1).

The following explanations of terms and methods are provided to better describe the present disclosure and to guide those of ordinary skill in the art in the practice of the present disclosure. The singular forms "a," "an," and "the" refer to one or more than one, unless the context clearly dictates otherwise. For example, the term "comprising a therapeutic agent" includes single or plural therapeutic agents and is considered equivalent to the phrase "comprising at least one therapeutic agent" or to the phase "comprising one or more therapeutic agents." The term "or" refers to a single element of stated alternative elements or a combination of two or more elements, unless the context clearly indicates otherwise. For example, the phrase "IL-1β or IL-18" refers to IL-1β, IL-18, or a combination of both IL-1β and IL-18. As used herein, "comprises" means "includes." Thus, "comprising A or B," means "including A, B, or A and B," without excluding additional elements.

Unless explained otherwise, all technical and scientific terms used herein have the same meaning as commonly understood to one of ordinary skill in the art to which this disclosure belongs. Although methods and materials similar or equivalent to those described herein can be used in the practice or testing of the present disclosure, suitable methods and materials are described below. The materials, methods, and examples are illustrative only and not intended to be limiting.

CFUs: colony-forming units
ICE: caspase-1/IL-1 Converting Enzyme
IL-1β: interleukin 1 beta
IL-18: interleukin 18
LT: anthrax lethal toxin Anthrax disease: The disease caused by the bacterium *Bacillus anthracis*. The disease can take on one of four forms: (1) Cutaneous, the most common, results from contact with an infected animal or animal products; (2) Inhalational is much less common and a result of spore deposition in the lungs, while (3) Gastrointestinal and (4) Oropharyngeal (back of the throat) are due to ingestion of infected meat. Cutaneous disease constitutes the majority (up to 95%) of anthrax cases. Anthrax usually develops in cattle, horses, sheep, and goats. Anthrax in humans is rare unless the spores are spread intentionally.

Anthrax disease occurs when spores enter the body, germinate to the bacillary form, and multiply. In cutaneous disease, spores gain entry through cuts, abrasions, or in some cases through certain species of biting flies. Germination is thought to take place in macrophages, and toxin release results in edema and tissue necrosis but little or no purulence, probably because of inhibitory effects of the toxins on leukocytes. Generally, cutaneous disease remains localized, although if untreated it may become systemic in up to 20% of cases, with dissemination via the lymphatics. In the gastrointestinal form, *B. anthracis* is ingested in spore-contaminated meat, and may invade anywhere in the gastrointestinal tract. Transport to mesenteric or other regional lymph nodes and replication occur, resulting in dissemination, bacteremia, and a high mortality rate. As in other forms of anthrax, involved nodes show an impressive degree of hemorrhage and necrosis.

The average incubation period for anthrax is 1 to 7 days, but it can take 60 days or longer for symptoms to develop. Symptoms depend on how the infection was acquired. For example, cutaneous anthrax has the following characteristics. Skin infection begins as a small, raised bump that might itch. Within 1 to 2 days, the bump develops into a fluid-filled blister about 1 cm (0.4 in.) to 3 cm (1.2 in.) in diameter. Within 7 to 10 days, the blister usually has a black center of dying tissue (eschar) surrounded by redness and swelling. The blister is usually painless. Additional blisters may develop.

*Bacillus anthracis* spore (or anthrax spore): A small reproductive body produced by *B. anthracis* bacteria. Such spores do not form normally during active growth and cell division. Rather, their differentiation begins when a population of vegetative cells passes out of the exponential phase of growth, usually as a result of nutrient depletion.

Anthrax toxin: An exotoxin produced by most strains of *Bacillus anthracis*, the causative agent of the disease anthrax. In its native form, the toxin consists of three heat-labile, antigenically distinct components: lethal factor (LF), protective antigen (PA) and edema factor (EF), which in concert lead to some of the clinical effects of anthrax. All three genes are encoded by the plasmid pXO1. Together, LF and PA constitute the lethal toxin (LT), and EF and PA the edema toxin.

Although the native anthrax toxin includes LF, PA, and EF, as used herein the term "anthrax toxin" can also refer to a toxin that does not include EF (that is, one that includes LF and PA (known as LT)).

Decrease: To reduce, for example to reduce the amount or other measure of activity of something, for example as compared to a control. When the term "decrease" is used herein, a 100% decrease is not required. Therefore, the term can refer to decreases of at least 20%, at least 40%, at least 50%, at least 60%, at least 75%, at least 80%, at least 90%, at least 95%, at least 98%, or even at least 100%. In particular examples, the amount of decrease is compared to a baseline or a control, such as a sample or subject not receiving a therapeutic agent.

Diagnose: To determine whether a subject has a disease or disorder, such as an anthrax disease. A disease can be diagnosed, for example, based on signs or symptoms associated with the disease, such as a laboratory result.

ICE (Caspase-1/IL-1 Converting Enzyme): An enzyme from the caspase family whose biological activity includes the ability to cleave the proforms of IL-1 µl and IL-18. This enzyme is a cysteine protease found in monocytes, lymphocytes, neutrophils, resting and activated T-lymphocytes, placenta tissue, and several B-lymphoblastoid cell lines. It is a heterodimeric protein composed of a 10 kDa and a 20 or 22 kDa subunit encoded by a common precursor of 45 kDa.

ICE nucleic acid and protein sequences for many species are known in the art. For example, ICE sequences are publicly available from GenBank Accession Nos. U04269 (mouse cDNA), AAA39306 (mouse protein), B027296 (pig cDNA), BAA89531 (pig protein), AF090119 (horse cDNA), Q9TV13 (horse protein), M87507 (human cDNA), and A42677 (human protein).

Methods for measuring an amount of ICE are known in the art, and include, but are not limited to, ELISA and Western blotting. Methods for measuring ICE activity are known in the art, and include, but are not limited to, measuring activity or an amount of activated IL-1β or IL-18.

ICE-dependent cytokine: A cytokine activated by ICE, for example by cleavage of the pro-form of the cytokine. Examples include IL-1β and IL-18.

ICE activity: Refers to the activity of ICE that induces disease in response to infection of a cell by a pathogen or portion thereof, such as the pathological effects of ICE in response to infection with anthrax (such as *B. anthracis* spores or anthrax LT). Such effects can be mediated by immunological, toxic, or other pathological mechanisms. Such activity may be induced by the activity of a biomolecule that is an upstream activator or ICE (such as anthrax LT), as well as the activity of a biomolecule that is activated by ICE, such as an ICE-dependent cytokine (for example IL-1β or IL-18).

Methods of decreasing ICE activity include, but are not limited to, reducing expression of ICE or an ICE-dependent cytokine protein or nucleic acid sequence (such as decreasing transcription or translation), as well as decreasing the interaction between a desired molecule and its target (such as anthrax LT).

Infect: The introduction of a pathogen (or a portion thereof) into an organism or cell, such as a cell of a subject. In a particular example, infection includes introduction of anthrax into a cell, or administration to a subject, such as in the form of *B. anthracis* spores or anthrax lethal toxin.

IL-1β (interleukin 1 beta): One of the two molecular forms of IL-1 (the other is IL-1 alpha). IL1-β is the predominant form in humans, while IL1-alpha is the predominant form in mice. IL-1β includes an IL-1β peptide or nucleic acid sequence from any organism, including variants, fragments, and fusions thereof that retain IL-1β biological activity. IL1-β is synthesized as a precursor of approximately 35 kDa (269 amino acids). The mature protein is generated by proteolytic cleavage by a number of proteases. One biological activity of IL-1β is the stimulation of T-helper cells, which are induced to secrete IL-2 and to express IL-2 receptors.

IL-1β nucleic acid and protein sequences for many species are known in the art. For example, IL-1β sequences are publicly available from GenBank Accession Nos. NM_000576 (human cDNA), NP_000567 (human protein), U19845 (rhesus monkey cDNA), AAA86709 (rhesus monkey protein), NM_001009465 (sheep cDNA), NP_001009465 (sheep protein), NM_008361 (mouse cDNA) and NP_032387 (mouse protein).

Methods for measuring an amount of IL-1β are known in the art, and include, but are not limited to, ELISA and Western blotting. Methods for measuring IL-1β activity are also known, and include measuring proliferation of the mouse helper T cell line D10.G4.1 (R&D Systems), for example in the presence of a cell supernatant or biological sample (such as serum or plasma).

IL-18 (interleukin 18): A proinflammatory cytokine that belongs to the IL-1 family of ligands. Also referred to in the literature as interferon-gamma inducing factor (IGIF). IL-18 is a potent inducer of interferon-gamma (IFN-γ) production by T-cells and NK cells. Either independently or in synergy with IL-12, the effects of IL-18, through its induction of IFN-gamma, can lead to a rapid activation of the monocyte/macrophage system with an upregulation of these cell's innate immune capabilities.

IL-18 is a 24 kDa, non-glycosylated polypeptide that lacks a classical signal sequence and possesses a structure recognizably similar to IL-1. IL-18 is synthesized as a bio-inactive propeptide that undergoes proteolytic cleavage by either ICE (interleukin-1 beta converting enzyme) or another caspase to generate a mature, bioactive, 18 kDa molecule. Cells known to express IL-18 include macrophages/Kupffer cells, keratinocytes, glucocorticoid-secreting adrenal cortex cells, and osteoblasts.

IL-18 includes an IL-18 peptide or nucleic acid sequence from any organism, including variants, fragments, and fusions thereof that retain IL-18 biological activity. IL-18 nucleic acid and protein sequences for many species are known in the art. For example, IL-18 sequences are publicly available from GenBank Accession Nos. NM_001562 (human cDNA), NP_001553 and CAG46771 (human protein), AF303732 (rhesus monkey cDNA), AAK13416 (rhesus monkey protein), NM_019165 (rat cDNA), NP_062038 (rat protein), AY628648 (chicken cDNA), AAT40993 (chicken protein), AY362457 (mouse cDNA) and AAQ63045 (mouse protein). The proteins from murine (192 amino acids) and human IL-18 (193 amino acids) sources show about 65% homology.

Methods for measuring an amount of IL-18 are known in the art, and include, but are not limited to, ELISA and Western blotting. In addition, Konishi et al. (*J. Immunol. Meth.* 209: 187-91, 1997) describe sensitive bioassays for human IL-18 activity using the human myelomonocytic cell line, KG-1.

LF (lethal factor): A 90 kD metalloprotease that cleaves the mitogen-activated protein kinase kinases (MAPKK), including MEK1, MEK2, MKK3, MKK4, MKK6 and MKK7 but not MEK5, thereby inhibiting the MAPK pathway. Lethal factor is pathogenic enzyme of anthrax.

Includes native LF nucleic acid and protein sequences, as well as variants, fragments, and fusions thereof that retain LF biological activity. Also includes recombinantly produced LF.

LT (anthrax lethal toxin): A multimer of protective antigen (PA) and lethal factor (LF). Also referred to in the art as LeTx. LT is a virulence factor for *Bacillus anthracis* whose biological activity includes the ability to proteolytically cleave and inactivate mitogen activated protein kinase kinases (MAPKKs) that propagate pro-survival signals in macrophages. In particular examples, LT is sufficient to induce many of the laboratory manifestations of anthrax disease in animal models (such as non-human primates and rodents).

Includes native LT nucleic acid and protein sequences, as well as variants, fragments, and fusions thereof that retain LT biological activity. Also includes recombinantly produced LT.

Pathogenicity or pathological activity of anthrax: The ability of *B. anthracis* or a portion thereof (such as a *B. anthracis* spore or anthrax LT) to inflict damage to a cell by any mechanism, for example to cause disease in a subject.

Pharmaceutical agent or drug: A chemical compound or composition capable of inducing a desired therapeutic or prophylactic effect when administered to a subject, alone or in combination with another therapeutic agent(s) or pharmaceutically acceptable carriers. In a particular example, a pharmaceutical agent decreases one or more symptoms of an anthrax infection.

Preventing or treating a disease: "Preventing" a disease refers to inhibiting the full development of a disease, for example preventing development of anthrax disease. Prevention of a disease does not require a total absence of infection. For example, a decrease of at least 50% can be sufficient. "Treatment" refers to a therapeutic intervention that ameliorates a sign or symptom of a disease or pathological condition, such a sign or symptom of anthrax disease. Treatment can also induce remission or cure of a condition, such as anthrax disease.

Protective antigen (PA): One of the three proteins that comprise the anthrax toxin, and one of the two proteins that constitute LT. PA is an 83 kD protein so named because it is the main protective constituent of anthrax vaccines. PA binds to the anthrax toxin receptor (ATR) on target cells and is then proteolytically cleaved by the enzyme furin of a 20 kd fragment. The smaller cleaved 63 kD PA remnant ($PA_{63}$) oligomerizes features a newly exposed, second binding domain and binds to either EF to form edema toxin, or LF to form lethal toxin (LT), and the complex is internalized into the cell. From these endosomes, the $PA_{63}$ channel enables translocation of LF and EF to the cytosol.

Includes native PA nucleic acid and protein sequences, as well as variants, fragments, and fusions thereof that retain PA biological activity. Also includes recombinantly produced PA.

Sample: A biological specimen, such as one that contains nucleic acid molecules (such as cDNA or mRNA), proteins, or combinations thereof. Exemplary samples include, but are not limited to: peripheral blood, plasma, serum, urine, saliva, tissue biopsy, pulmonary washings, expectorated sputum, surgical specimen, amniocentesis samples and autopsy material. In one example, a sample includes peripheral blood mononuclear cells (PBMCs).

Subject: Living multi-cellular vertebrate organisms, including human and veterinary subjects. Particular examples of veterinary subjects include domesticated animals (such as cats and dogs), livestock (for example, cattle, horses, pigs, sheep, and goats), laboratory animals (for example, mice, rabbits, rats, gerbils, guinea pigs, and non-human primates), as well as birds, reptiles, and fish.

Test agent: A candidate agent (including chemical compounds and compositions, as well as biological agents) that is tested to determine its activity, such its activity on anthrax infection or a symptom of anthrax disease.

Therapeutically Effective Amount: An amount of a pharmaceutical preparation that alone, or together with a pharmaceutically acceptable carrier or one or more additional therapeutic agents, induces the desired response. The preparations disclosed herein are administered in therapeutically effective amounts.

In another or additional example, it is an amount sufficient to partially or completely alleviate symptoms of anthrax infection within a subject. Treatment can involve only slowing the progression of the infection temporarily, but can also include halting or reversing the progression of the infection permanently. For example, a pharmaceutical preparation can decrease one or more symptoms of anthrax, for example decrease a symptom by at least 20%, at least 50%, at least 70%, at least 90%, at least 98%, or even at least 100%, as compared to an amount in the absence of the pharmaceutical preparation.

Effective amounts a therapeutic agent can be determined in many different ways, such as assaying for a reduction in the rate of infection of cells or subjects or improvement of physiological condition of an infected subject. Effective amounts also can be determined through various in vitro, in vivo or in situ assays, including the assays described herein.

Therapeutic agents can be administered in a single dose, or in several doses, for example daily, during a course of treatment. However, the effective amount of can be dependent on the source applied (for example a vaccine isolated from a cellular extract versus a chemically synthesized and purified vaccine), the subject being treated, the severity and type of the condition being treated, and the manner of administration.

Bioassays

Based on the observation that anthrax LT induces activation of ICE, which leads to the activation of ICE-dependent cytokines and their extracellular release, bioassays for anthrax activity are provided. Such assays can be used to determine whether a test agent can potentially treat a subject having an anthrax infection or protect a subject from infection in the future (prophylaxis). Therefore, the disclosed assays can be used to identify test agents that can decrease the pathogenicity of anthrax. Such assays can be conduced in vitro, such as using cells in culture, or in vivo, for example using a laboratory animal.

In one example, the method includes contacting a cell expressing ICE with one or more test agents (such as at least one test agent, at least two test agents, or at least three test agents). Subsequently, whether ICE activity is reduced in the cell is determined, wherein a decrease in ICE activity indicates the test agent decreases pathogenicity of anthrax, for example by decreasing the biological activity of $B.$ $anthracis$ spores or anthrax LT. In particular examples, the cell expressing ICE is infected with anthrax, for example infected with $B.$ $anthracis$ spores or exposed to anthrax toxin (for example anthrax LT), wherein anthrax infection activates ICE.

In one example, ICE activity is determined by measuring the biological activity of activated ICE, for example by measuring activity of an ICE-dependent cytokine, such as the activity of activated IL-1β or activated IL-18. In a specific example, ICE activity is determined by measuring an amount of activated ICE or ICE-dependent cytokine present. For example, an amount of extracellular activated ICE-dependent cytokine, such as activated IL-1β or activated IL-18, released into the cell culture medium can be determined. In another example, an amount of intracellular ICE or ICE-dependent cytokine (such as IL-1β or IL-18), for example determining the amount of pro- or active-form of the protein, is measured by determining an amount of intracellular ICE or ICE-dependent cytokine (such as the pro- or active-form) present. In particular examples, ICE biological activity is not determined. In some examples, activated ICE-dependent cytokine biological activity is measured, such as activated IL-1β or IL-18 biological activity. Methods for determining whether a particular protein is present intracellularly or extracellularly are known in the art.

In particular examples, the method further includes comparing the observed ICE activity (such as the functional activity or amount of activated ICE or activated ICE-dependent cytokine, for example activated IL-1β or activated IL-18) in the presence of the test agent to ICE activity in the absence of the test agent. For example, the observed ICE activity in the presence of the test agent can be compared to an established baseline or a reference standard. In another example, the observed ICE activity is compared to ICE activity in the presence of a control, such as a positive or negative control.

An example of a positive control is one that contains an amount of ICE activity (such as the functional activity or amount of activated ICE or activated ICE-dependent cytokine, for example activated IL-1β or activated IL-18) present in anthrax-infected cells exposed to an agent known to decrease anthrax pathogenicity (such as ciprofloxacin hydrochloride or a neutralizing antibody to anthrax LT). For example, the control can include an amount of activated ICE or an ICE-dependent cytokine (such as an amount of activated IL-1β or IL-18). When comparing the ICE activity present in the experimental to the positive control, similar ICE activity relative to the positive control indicates the test agent decreases pathogenicity of anthrax. For example, a test agent that results in ICE activity (such as the functional activity or amount of activated ICE or activated ICE-dependent cytokine, for example activated IL-1β or activated IL-18) that is similar to that observed in the positive control, such as a difference of no more than 20%, no more than 10%, or no more than 5%, can be used in particular examples to treat an anthrax infection (for example to reduce systemic shock or inflammation) or to inhibit (such as prevent) anthrax infection.

An example of a negative control is one that contains an amount of ICE activity (such as the functional activity or amount of activated ICE or activated ICE-dependent cytokine, for example activated IL-1β or activated IL-18) present in anthrax-infected cells contacted with an agent known to not affect anthrax pathogenicity. For example, the control can include an amount of activated ICE or an ICE-dependent cytokine (such as an amount of activated IL-1β or IL-18) present when no potentially therapeutic test agent is included. When comparing the ICE activity present in the experimental to the negative control, decreased ICE activity relative to the negative control indicates the test agent decreases pathogenicity of anthrax. For example, a test agent that decreases or eliminates ICE activity (such as the functional activity or amount of activated ICE or activated ICE-dependent cytokine, for example activated IL-1β or activated IL-18) in the cell (such as decreases the activation of ICE or an ICE-dependent cytokine such as IL-1β or IL-18) compared to the negative control, such as a decrease of at least 10%, at least 50%, at least 90%, or even at least 99% as compared to the negative control, can be used in particular examples to treat an anthrax infection or to inhibit (such as prevent) anthrax infection.

To determine if a test agent can inhibit (including prevent) anthrax infection, the following exemplary methods can be used. One or more test agents are contacted with a cell in vitro, and the cells infected subsequently (or at the same time as the test agent) with anthrax (such as $B.$ $anthracis$ spores or anthrax LT). In one example, the cells are infected with anthrax and contacted with the test agent simultaneously. In another example, the cells are infected with anthrax at least 5 minutes after contact with the test agent, such as at least 10 minutes, at least 30 minutes, at least 60 minutes, or even at least 120 minutes after contacting the cells with the test agent. In some examples, multiple time points are determined. Following infection with anthrax, ICE activity is determined, such as at least 15 minutes, at least 30 minutes, at least 60 minutes, at least 2 hours, or even at least 24 hours following infection. In some examples, multiple time points are determined. Methods of determining ICE activity include, but are not limited to, measuring functional activity of ICE, for example by determining the functional activity of an ICE-dependent cytokine (such as activated IL-1β or activated IL-18); and measuring an amount of activated ICE or activated ICE-dependent cytokine (such as an amount of activated IL-1β or activated IL-18). The method can further include comparing ICE activity to a control, such as a positive or negative control. Agents that decrease ICE activity (such as those that decrease ICE or ICE-dependent cytokine activity or decrease an amount of ICE or ICE-dependent cytokine) can be useful, for example, in decreasing or even inhibiting anthrax infection. ICE functional activity can be determined, for example, by measuring the effectiveness of ICE in activating ICE-dependent cytokines. For example, levels of ICE can remain substantially unchanged, but the functional activity of ICE can be decreased by an agent that decreases an enzymatic or other activity of ICE.

Methods are also provided to determine if a test agent can treat an anthrax infection, such as infection with *B. anthracis* spores or exposure to LT. In particular examples, the method includes contacting a cell with one or more test agents, wherein the cell expresses ICE. In particular examples, the method includes infecting cells with anthrax and subsequently contacting the cell with one or more test agents. In some examples, the cells are contacted with the test agent at least 5 minutes after infection, such as at least 10 minutes, at least 30 minutes, at least 60 minutes, or even at least 120 minutes after anthrax infection. In one example, multiple time points are determined. Following incubation with the one or more test agents, ICE activity is determined (for example pathogenic activity), such as at least 15 minutes, at least 30 minutes, at least 60 minutes, at least 2 hours, or even at least 24 hours following anthrax infection. In some examples, multiple time points are determined. Methods of determining ICE activity include, but are not limited to, measuring activity of ICE, for example determining the activity of an ICE-dependent cytokine (such as activated IL-1β or activated IL-18); and measuring an amount of activated ICE or activated ICE-dependent cytokine (such as an amount of activated IL-1β or activated IL-18). The method can further include comparing ICE activity to a control. Agents that decrease ICE functional activity (such as those that decrease ICE or ICE-dependent cytokine activity or decrease an amount of ICE or ICE-dependent cytokine) can be useful, for example, in treating an anthrax infection (for example reducing one or more symptoms of systemic shock).

In particular examples, a cell in culture is infected with $10^4$-$10^8$ *B. anthracis* spores/ml having an MOI of about 1:1), for example for at least 30 minutes, at least one hour, at least four hours, at least six hours, or even for at least 24 hours. In other examples, the cell is infected with anthrax LT for at least 10 minutes, at least 30 minutes, at least one hour, at least four hours, at least six hours, or even for at least 24 hours. Exemplary amounts of LT include, but are not limited to, a ratio of at least 1:1 of PA:LF, for example 2:1 PA:LF, 2.5:1 PA:LF, or even 4:1 PA:LF.

In particular examples, the disclosed methods are performed in vivo. In such examples, the cell expressing ICE and contacted with the test agent is present in a subject. Similarly, in examples where the cell is infected with anthrax, the cell is present in a subject and the subject infected with anthrax. Exemplary subjects include, but are not limited to, a laboratory animal, such as a non-human primate (for example a rhesus macaque or cynomolgus macaque) or other mammals, such as a rodent (for example a rat, mouse, rabbit, or guinea pig). In a specific example, the subject is a human subject. In such in vivo examples, the methods described above can be used, wherein contacting one or more test agents with a cell includes administering the test agent(s) to the subject, infecting the cell with anthrax includes infecting the subject with anthrax, and determining ICE activity includes determining whether ICE activity is decreased in the subject, such as in a cell, serum, or plasma from the subject.

In particular examples determining ICE activity in the subject includes determining the functional activity of activated ICE, for example by determining the activity of an activated ICE-dependent cytokine (such as the activity of activated IL-1β or IL-18) present in a sample obtained from the subject. The ICE activity that is measured is a measure of potential biological activity that ICE can induce. In a particular example, determining ICE activity in the subject includes determining an amount of activated ICE or an activated ICE-dependent cytokine (such as the amount of activated IL-1β or IL-18) present in a sample obtained from the subject. For example, extracellular amounts of activated IL-1β or IL-18 can be determined from a serum or plasma sample obtained from the subject. In another example, the intracellular amount of pro- or active-forms of ICE or an activated ICE-dependent cytokine (such as the amount of activated IL-1β or IL-18) are determined from a sample obtained from the subject that includes cells. Examples of such samples include, but are not limited to, blood, tissue biopsy, or oral swab.

Cells

Cells that can be used in the disclosed bioassays, for example when the bioassay is an in vitro assay, are known. Ideally, the cells used are susceptible to anthrax infection, express ICE, and show an increase in ICE activity (such as ICE or ICE-dependent cytokine activity, or an amount of ICE or ICE-dependent cytokine present) following exposure to anthrax, for example in the form of *B. anthracis* spores or anthrax LT.

In one example, the cell is a macrophage, such as a commercially available cell line or a primary cell line derived from a subject. In a specific example, the cell is a dendritic cell. For example, the mouse macrophage cell lines J744A.1 and RAW264.7, and the human U-937 and THP-1 cell lines (available from American Type Culture Collection) can be used.

The cell, such as a macrophage, can also be obtained from a subject. Methods for purification of macrophages from blood are known. In one example, mononuclear cells are obtained by apheresis, and the monocytes enriched by centrifugal elutriation. The resulting monocytes can be differentiated into dendritic cells, using methods known in the art. Briefly, monocytes are grown in the presence of granulocyte-macrophage colony-stimulating factor (GM-CSF), for example at a concentration of 800 U/ml, and IL-4 (for example at 500-U/ml). Non-adherent cells are harvested after 5 days, and the cells plated in the presence of GM-CSF (such as at $10^6$ cells/ml with 800 U/ml GM-CSF).

In another example, peritoneal macrophage cells are obtained, for example from a BALB/c or C57BL/6 mouse, using methods known in the art. Briefly, mice are injected with 3% Brewer's thioglycolate (Sigma) for 3 to 5 days, after which mice are euthanized (for example with $CO_2$) and the peritoneal cavity lavaged with 10 ml of sterile saline. This results in >95% macrophages. Cells can be washed and resuspended in DMEM-10% FCS at $5\times10^5$/ml.

In one example, alveolar macrophages (AM) are used. For example, THP-1 cells differentiated with phorbol ester can be used as a model for human AM. Briefly, THP-1 cells (American Type Culture Collection), for example at a concentration of $5\times10^5$/ml, are differentiated with 20 nM 12-0 tetradecanoylphorbol 13-acetate (PMA) (for example in DMEM with 10% FCS. Human AM can be prepared using known methods. Briefly, a human subject undergoes a bronchoscopy with bronchoalveolar lavage with 100 ml of saline. Fluid is filtered to remove debris. Cells are spun at 800×g for 5 minutes and resuspended in DMEM plus 10% FCS (for example at $5\times10^5$/ml).

Test Agents

Exemplary test agents include, but are not limited to, any peptide or non-peptide composition in a purified or non-purified form, such as peptides made of D- and/or L-configuration amino acids (in, for example, the form of random peptide libraries; see Lam et al., *Nature* 354:82-4, 1991), phosphopeptides (such as in the form of random or partially degenerate, directed phosphopeptide libraries; see, for example, Songyang et al., *Cell* 72:767-78, 1993), nucleic acid molecules, antibodies (such a monoclonal, polyclonal, chimeric, and humanized antibodies, or a fragment thereof), and small or large organic or inorganic molecules such as aromatics, fatty acids, and carbohydrates. A test agent can also include a complex mixture or "cocktail" of molecules.

In a particular example for use in vivo, a test agent is a vaccine preparation (for example a peptide and an adjuvant). The vaccine can be administered at least once prior to infection with anthrax, such as one, two, three or even four doses. The animal can then be subsequently infected with *B. anthracis* spores of anthrax toxin, such as at least one week, at least 2 weeks, at least 4 weeks, at least 6 weeks, at least 8 weeks, at least 10 weeks, at least 12 weeks, at least 6 months, or even at least 1 year following administration of the vaccine.

In a particular example, a test agent is an agent that decreases ICE functional activity (for example ICE-dependent cytokine activity, or an amount of activated ICE or activated ICE-dependent cytokine present). Such agents can include those that decrease transcription or translation of ICE or an ICE-dependent cytokine (such as IL-1β or IL-18). Examples of such agents include, but are not limited to, an siRNA, antisense, microRNA, or ribozyme molecule that recognizes an ICE or an ICE-dependent cytokine (such as IL-1β or IL-18) nucleic acid sequence. Other examples of such agents include, but not limited to, as well as those that decrease binding of ICE or an ICE-dependent cytokine to its target (such as a specific binding agent, for example an antibody, that specifically recognizes and binds to ICE, IL-1β, or IL-18). In a particular example, the test agent is a protein inhibitor (a receptor antagonist), such as Kineret® (anakinra) (Amgen, Thousand Oaks, Calif.) which is an inhibitor of IL-1β. In another example, the test agent is a neutralizing antibody, such as those available from R&D Systems that recognize IL-1β and IL-18 and their receptors. In yet another example, the test agent is a binding protein, such as the IL-18 binding protein (which binds and neutralizes IL-18 activity) available from R&D Systems (number D0044-3).

Anthrax Spores and Toxin

*B. anthracis* spores are available in nature and can be produced using methods in the art. For example, spores from *B. anthracis* strain 7702 (pXO1$^+$ pXO2$^-$) that produces LT but not a capsule, and the Sterne strain that produces LT (34F2; Colorado Serum Company), can be used. Other examples are provided in Table 1.

TABLE 1

| Exemplary *B. anthracis* strains and their county of origin | | |
|---|---|---|
| Animal isolates | Human isolates | Other isolates |
| ASIL K0778/Canada | ASIL K4539/France | 33/South Africa[a] |
| ASIL K1963/Canada | BA1017/Haiti | ASIL K1769/South Africa[b] |
| ASIL K6286/Canada | ASIL K5926/India | |
| BA0018/Canada | ASIL K6387/India | BA1024/Ireland[c] |
| ASIL K6093/Croatia | BA1023/Pakistan | |
| ASIL K7282/Germany | ASIL K7038/South Korea | |
| ASIL K1938/Indonesia | | |
| ASIL K4241/Italy | 28 Ohio ASB/USA | |
| ASIL K4849/Mozambique | BA1086/Zimbabwe | |
| ASIL K7978/Namibia | | |
| ASIL K1671/Norway | | |
| ASIL K8091/Norway | | |
| BA1003/South Africa | | |
| BA1018/South Africa | | |
| BA1031/South Africa | | |
| ASIL K3519/Tanzania | | |
| ASIL K9729/Turkey | | |
| Ames/USA | | |
| ASIL K2087/USA | | |
| BA1007/USA | | |

TABLE 1-continued

| Exemplary *B. anthracis* strains and their county of origin | | |
|---|---|---|
| Animal isolates | Human isolates | Other isolates |
| Texas-2/USA | | |
| BA1002/Vollum 1B | | |

[a]Unknown origin.
[b]Environment isolate.
[c]Textile isolate.

Spores can be prepared by any method used in the art (for example see Finlay et al. *Food Microbiol.* 19:431-9, 2002). Although particular examples are provided herein, the disclosure is not limited to these methods. For example, a particular culture method may be used when producing spores from a particular strain of *B. anthracis*. In one example, the following method is used. Briefly, nutrient agar plates are inoculated with overnight cultures of the desired *B. anthracis* strain and incubated overnight at the appropriate temperature. Resulting colonies are used to inoculate 2 ml nutrient broth cultures, which are grown overnight at the appropriate temperature with shaking. An aliquot of the culture is spread onto nutrient agar plates containing 5 µg/ml MnSO$_4$, and incubated at the appropriate temperature overnight, followed by incubation at room temperature for 48 hours in the dark. Colonies are scraped from the surface of the agar and suspended in distilled water and prior to infection (such as infection of a cell or subject) can be heat treated at 65° C. for 30 minutes to kill any remaining vegetative cells. Spore material can also be purified by centrifugation through 58% (vol/vol) Renografin (Renocal-76; Bracco Diagnostics, Princeton, N.J.) prior to infection.

In another example, the following method is used. Spores are allowed to germinate overnight at 37° C. (for example in phage assay broth that includes 8 mg of Difco nutrient broth, 0.15 mg of CaCl$_2$, 0.2 mg of MgSO$_4$, 0.05 mg of MnSO$_4$, 5 mg of NaCl, 10% horse serum). Flasks are incubated at 30° C. for 3 to 5 days. Spores are centrifuged and washed with sterile H$_2$O, resuspended in sterile H$_2$O and heat treated at 65° C. for 30 minutes to kill any vegetative spores.

The purified spore pellet can be washed with cold distilled water and stored at 4° C. The purity of the spores can be determined using Modified Ziehl-Neelsen staining. A viability count can be performed on the spore preparation, and the preparation adjusted to the desired concentration (such as 10$^6$ to 10$^{10}$ CFU/ml or 10$^6$ to 10$^{10}$ spores/ml).

As an alternative (or in addition) to using spores, anthrax toxin can be contacted with the cells. In one example, a purified tripartite exotoxin is used. In another example, a combination of LF and PA is used. Recombinant PA and LF are commercially available (see Example 1). The physiological receptor binding ratio is 7 PA molecules to 3 LF molecules. However other ratios can be used. Exemplary ratios of PA:LF include, but are not limited to, at least 1:1 PA:LF, at least 2:1 PA:LF, at least 2.5:1 PA:LF, or even at least 4:1 PA:LF. In a particular example, at least 0.001 µg/ml LF and at least 0.001 µg/ml of PA are contacted with the cells, such as at least 0.01 µg/ml LF and at least 0.01 µg/ml of PA, at least 0.1 µg/ml LF and at least 0.1 µg/ml of PA, or at least 1 µg/ml LF and at least 1 µg/ml of PA. In another particular example, at least 10 µg LF and at least 10 µg of PA are administered to a subject, such as at least 50 µg LF and at least 50 µg of PA, or at least 100 µg LF and at least 100 µg of PA. In yet another example, at least 0.01 µg LF per g of subject (µg/g) and at least 0.01 μg/g of PA are administered to a subject, such as at least 0.1 μg/g LF and at least 0.1 μg/g of PA, or at least 0.5 μg/g LF and at least 0.5 μg/g of PA.

Measuring ICE Activity

Methods for determining ICE activity (including pathological activity) are known in the art. For example, ICE activity can be determined by measuring the functional activity of activated ICE or an activated ICE-dependent cytokine, such as the activity of activated IL-1β or activated IL-18. In another example, ICE activity is determined by measuring an amount of activated ICE or ICE-dependent cytokine present. For example, an amount of activated intracellular ICE or ICE-dependent cytokine present can be determined, for example by Western blotting of active-forms of ICE or an ICE-dependent cytokine. In another example, an amount of extracellular activated IL-1 or activated IL-18 protein released by the cell (for example into the culture medium or into the plasma of a subject) is determined. For example, the presence of IL-1β or IL-18 proteins in the culture supernatant (extracellular proteins) can be determined, for example using ELISA (for example see Example 1) or Western blotting.

In one example, antibodies specific for ICE-dependent cytokines (such as IL-1β and IL-18) permit detection of these proteins in the supernatant. For example, incubation of the cell supernatant with the antibodies permits formation of protein-antibody complexes. The presence of such complexes can be determined using methods known in the art. For example, the antibody can include a detectable label, such as a fluorophore, radiolabel, or enzyme, which permits detection of the antibody, for example using ELISA. In particular examples, multiple antibodies (each with a unique detectable label) are incubated with the supernatant, and the presence of multiple complexes detected simultaneously.

In a particular example, Western blotting is used to detect the presence of extracellular activated ICE-dependent cytokines (such as IL-1β or IL-18), such as those present in a cell culture supernatant or those present in an extracellular fluid of a subject (such as serum or plasma). Briefly, the cell supernatant or extracellular fluid is resolved by SDS-PAGE, and the proteins transferred to an appropriate medium, such as nitrocellulose. The nitrocellulose is incubated with the appropriate antibody (which itself can have a label, or which can be detected by using the appropriate labeled secondary antibody), which permits detection of the antibody-protein complex.

In another example, a colorimetric assay is used to detect the presence of extracellular activated ICE-dependent cytokines (such as IL-1β or IL-18) present in a solution, such as those present in a cell culture supernatant or in an extracellular fluid of a subject (such as serum or plasma). Briefly, the cell supernatant or extracellular fluid is exposed to a material that will produce a colorimetric reaction if an activated ICE-dependent cytokine is present, for example at a particular concentration.

The presence of intracellular activated ICE or an activated ICE-dependent cytokine (such as IL-1β or IL-18) can also be detected to determine ICE activity. For example, Western blotting of cell lysates can be used to determine an amount of activated ICE or an activated ICE-dependent cytokine present in a cell. Briefly, cells are lysed (for example by using a detergent), and the resulting supernatant incubated with one or more antibodies that specifically recognize the pro-form or the active-form or ICE or an ICE-dependent cytokine (such as IL-1β or IL-18). The resulting protein-antibody complex can be detected as described above. In another example, microscopy or flow cytometry is used to determine an amount of pro-form or active-form or ICE or an ICE-dependent cytokine present in a cell.

In addition to the methods described above, ICE activity can be measured by other methods known in the art. For example, quantitative mass spectroscopy can be used to quantitate an amount of activated ICE or ICE-dependent cytokine (such as IL-1β or IL-18) present intracellularly or extracellularly.

Antibodies that are specific for ICE and ICE-dependent cytokines (such as IL-1β or IL-18) are known in the art (see Examples 1 and 2). In addition, antibodies that can distinguish between the active-form of such proteins and the pro-form of such proteins are known.

In addition to the above methods, other bioassays permit detection of the biological functional activity, or amount of, IL-1β or IL-18 present. For example, IL-18 induces IFN-γ production in a myelomonocytic cell line, KG-1. In addition, IL-1β induces proliferation of the mouse helper T cell line D10.G4.1 (R&D Systems). Therefore, exposure of cell supernatants to KG-1 or D10.G4.1 cell lines can be used to determine a functional activity of IL-18 or IL-1β produced, respectively, by determining the activity or amount of IFN-γ produced or an amount of proliferation, respectively.

In examples where the bioassay is an in vivo assay, a sample is obtained from the subject, and the ICE activity in the subject determined using the methods described above. For example, a serum or plasma sample can be used to measure ICE activity present extracellularly, such as amount of ICE-dependent cytokine (such as IL-1β or IL-18) present in the subject (for example by using ELISA or Western blotting as described above). In another example, a sample containing whole cells is obtained from the subject (such as a tissue biopsy, oral swab, or a blood sample containing white blood cells). The cells in the sample are lysed, and the resulting lysates analyzed for the presence of active-forms of intracellular ICE or an ICE-dependent cytokine (such as IL-1β or IL-18) (for example as described above using Western blotting).

Methods of Diagnosing Anthrax

Methods are provided for diagnosing anthrax infection in a subject. Examples of anthrax infection include infection with *B. anthracis* (or spores thereof), as well as exposure to anthrax toxin, such as LT. In particular examples, the method includes detecting ICE immunopathogenic activity, wherein an increase in ICE immunopathogenic activity indicates that the subject has an anthrax infection or has been exposed to anthrax spores or LT.

Methods for determining ICE immunopathogenic activity are described herein. For example, ICE immunopathogenic activity can be determined by measuring a quantity or functional activity of ICE, for example by detecting levels of ICE or an ICE-dependent cytokine (such as IL-1β or IL-18) present in the subject, wherein an increase in such an a quantity or functional activity of ICE indicates that the subject is infected with anthrax (or has been exposed to anthrax spores or LT). Methods for determining an amount of ICE or an ICE-dependent cytokine are known in the art, and particular examples are described above. In one example, ICE immunopathogenic activity present in the subject is determined using a biological sample from the subject, such as a blood or serum sample.

In particular examples, ICE immunopathogenic activity present in the subject is compared to a control. Particular examples of controls include negative controls (such as a sample that includes a reference amount of ICE immunopathogenic activity expected when a subject is not infected with, or exposed to, anthrax), and positive controls (such as a sample that includes a reference amount of ICE immunopathogenic activity expected when a subject is infected with, or exposed to, anthrax). When comparing ICE immunopathogenic activity present in the subject to a negative control, an increase in ICE immunopathogenic activity compared to the control indicates that the subject is infected with anthrax. Examples of such increases include an increase of at least 20%, at least 50%, or even at least 95% relative to the negative control. When comparing ICE immunopathogenic activity present in the subject to a positive control, a decrease in ICE immunopathogenic activity compared to the positive control indicates that the subject is not infected with anthrax. Examples of such decreases include a decrease of at least 20%, at least 50%, or even at least 95% relative to the positive control.

Methods of Treating Anthrax

Methods are provided for treating an anthrax infection, such as a subject infected with *B. anthracis* (or spores thereof) or exposed to anthrax toxin (such as LT). Such methods can be used to reduce one or more symptoms associated with anthrax infection, such as systemic shock, fever, inflammation, or blisters on the skin. In particular examples, the method includes decreasing ICE immunopathogenic activity in the subject, such as in the macrophages of the subject. For example, ICE immunopathogenic activity can be decreased by impairing a function or reducing an amount of ICE or a biomolecule that is an upstream activator or ICE (such as anthrax LT) or a downstream biomolecule that is activated by ICE (for example an ICE-dependent cytokine, such as IL-1β or IL-18) and involved in the pathogenicity of anthrax. In specific examples, the method includes decreasing the biological activity or amount of activated IL-1β or IL-18 present in the subject.

EXAMPLE 1

Anthrax Lethal Toxin Induces Production of IL-1β and IL-18 In Vitro

This example describes in vitro methods used to demonstrate that IL-1β and IL-18 are activated following exposure of cells to anthrax lethal toxin (LT).

Cytokine production was determined in two murine macrophage cell lines known to be sensitive to anthrax LT, RAW 264.7 and J774A.1 (American Type Culture Collection, Manassas, Va.). Cells were cultured in DMEM medium containing 10% FBS (Hyclone, Logan, Utah) and 1% Pen-Strep (Biosource International, Camarillo, Calif.) on low-attachment 24 well plates (Corning, Inc., Corning, N.Y.) at a concentration of 1-2 million cells/ml. Cell viability was assessed by trypan blue staining followed by enumeration using a hemocytometer. Only cultures with >99% viability were used.

Cells were treated with anthrax LT at a fixed concentration of 1 μg/ml lethal factor (LF) and 2.5 μg/ml of protective antigen (PA). This dose was toxic for both cell lines within 24 hours. Recombinant anthrax PA and LF (List Biological Laboratories, Inc., Campbell, Calif.) were stored as 1 mg/ml stock solutions in 1:1 glycerol: water. The endotoxin levels present in the PA and LF preparations from a representative lot using the company's manufacturing process were reported to be 11.9 EU/mg and 12.4 EU/mg, respectively (List Biological Laboratories, Inc., lot testing data).

Supernatants were collected following 24 hours of treatment and analyzed for production of pro-inflammatory cytokines produced by activated macrophages as follows. IL-1α, IL-1β, IL-6, IL-18 and TNF-α cytokine levels were determined by ELISA using commercial ELISA kits (R & D Systems). Cell-free supernatants were harvested after cell centrifugation and assayed neat or diluted according to the manufacturer's protocol. Absorbance readings were performed using a microplate reader (Dynatech Laboratories, Chantilly, Va.). Each culture was assayed in duplicate and averaged. Results were expressed as a ratio of cytokine levels in treated versus untreated cells.

Figure 1A:
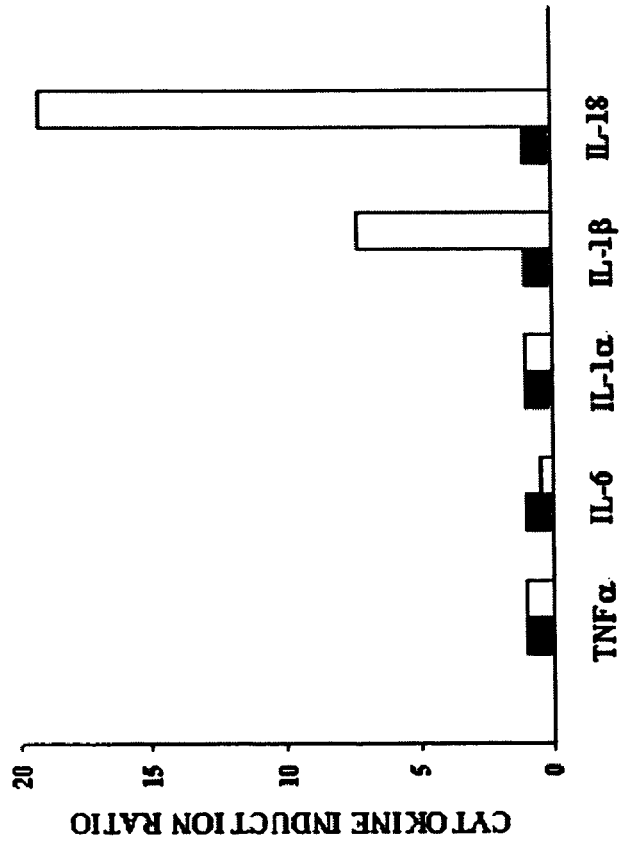

As shown in FIGS. 1A and 1B, anthrax LT did not increase the extracellular levels of TNF-α, IL-1α, and IL-6 produced by either RAW264.7 or J774A.1 cells. However, levels of IL-1β and IL-18 were increased by anthrax LT treatment in both cell lines. Extracellular levels of IL-1β and IL-18 in anthrax LT-treated RAW264.7 cells were 7-fold and 19-fold greater than baseline levels, respectively. The relative inductions of IL-1β (16-fold) and IL-18 (32-fold) were even higher in J774A.1 cells, although the absolute levels of induced IL-1β and IL-18 were lower in this cell line. Plateau levels of induced IL-1β and IL-18 were observed at an anthrax LF doses starting at 0.1 μg/ml for both RAW264.7 cells (FIGS. 2A and 2B) and J774A.1 cells.

Figure 2B:
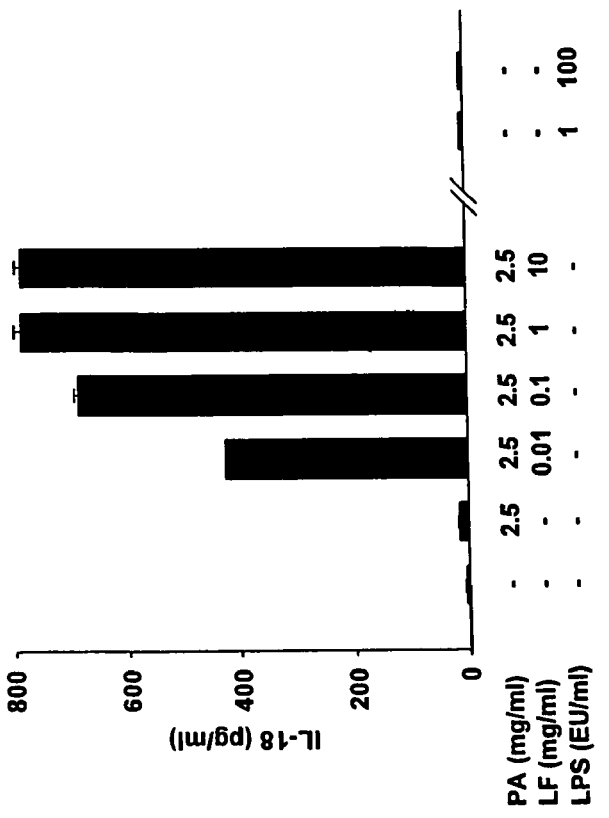
FIGS. 2A and 2B are bar graphs showing dose-dependent cytokine induction of IL-1β (A) and IL-18 (B) by LT in RAW264.7 cells. Each bar represents the average concentrations from duplicate ELISA assays. Shown is one representative experiment of four separate experiments. Bars indicate intra-assay standard deviation.
Figure 2A:
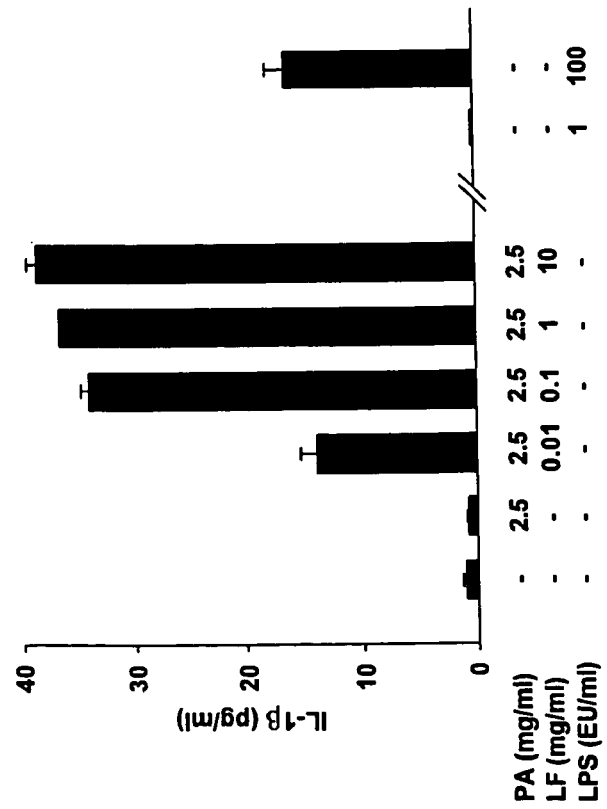

Both components of the anthrax LT were recombinant proteins generated in bacterial cell lines. To demonstrate that the observed effect was not due to endotoxin contamination, the following methods were used. RAW264.7 cell cultures were treated with increasing concentrations of anthrax LF as shown. Anthrax PA was administered at a constant, non-limiting dose of 2.5 μg/ml. Extracellular levels of IL-1β (FIG. 2A) and IL-18 (FIG. 2B) were measured by ELISA in duplicate 24 h following treatment. As a control, selected cultures received varying doses of LPS as indicated. As shown in FIGS. 2A and 2B, PA alone or LF alone did not induce IL-1β or IL-18. Moreover, residual levels of endotoxin in the anthrax LT components were extremely low (PA: 11.9 EU/mg and LF: 12.4 EU/mg). Even at the highest dose of anthrax LT used (PA: 2.5 μg/ml and LF: 10 μg/ml), the levels of residual LPS were at a maximum 0.15 EU/ml (FIGS. 2A and 2B). By comparison, lipopolysaccharide (LPS) doses of ≧100 EU/ml were needed for induction of IL-1β comparable to that resulting from anthrax LT treatment (FIG. 2A). IL-18 was not induced in RAW264.7 cells even at this dose (FIG. 2B). These observations demonstrate that the inductions of IL-1β and IL-18 by anthrax LT were not due to contaminating endotoxin in the toxin preparations, but were instead an effect of anthrax LT.

EXAMPLE 2

Anthrax LT Leads to Proteolytic Activation of ICE In Vitro

As described in Example 1, exposing cells to anthrax LT led to the extracellular accumulation of the cytokines IL-1β and IL-18, but not other pro-inflammatory cytokines. IL-1β and IL-18 are both processed by ICE, an enzyme from the caspase family that cleaves the proforms of both of these molecules. These cleavage products of IL-1β and IL-18 are secreted into the extracellular environment in their bioactive form (Dinarello and Fantuzzi, *J. Infect. Dis.* 187 Suppl 2:S370-384, 2003). As this upstream processing pathway is a common feature shared between IL-1β and IL-18, but not the other cytokines examined, this example describes in vitro methods used to demonstrate that anthrax LT treatment leads to activation of ICE.

Lysates from anthrax LT-treated RAW264.7 and J774A.1 cells (see Example 1) were collected and analyzed by Western blotting for the presence of the cleaved ICE as follows. Cell pellets were lysed on ice for 45 minutes in a buffer containing 20 mM Tris Cl, 150 mM NaCl, 5 mM EDTA, 2.5 mM sodium pyrophosphate, 1 mM $Na_3VO_4$, 1% Triton-X-100, and a protease inhibitor cocktail (Sigma, St. Louis, Mo.). Protein extracts were generated from centrifuged lysates, and 50 μg was loaded on a 4-12% NuPage gradient gel (Invitrogen, Carlsbad, Calif.). These protein extracts were electrophoretically separated and then transferred to 0.2 μm nitrocellulose membranes (Bio-Rad, Hercules, Calif.).

Western blotting was performed using standard techniques (Bacon et al., *J. Exp. Med.* 181:399-404, 1995). The following primary antibodies were used for Western blotting assays: rabbit polyclonal anti-caspase-1 (1:100 BD Apotech, San Diego, Calif.), IL-1β (1 μg/ml, Upstate Group, Inc., Lake Placid, N.Y.), and mouse monoclonal anti-actin IgM (1:10,000, Oncogene Research Products, San Diego, Calif.). Polyclonal anti-rabbit IgG-HRP (1:2000, Amersham Biosciences, Piscataway, N.J.) and anti-mouse IgM-HRP (1:3000, Oncogene Research Products) were used as secondary antibodies.

Upon activation, the proform of ICE (p45) is ultimately cleaved into the two bioactive forms p20 and p10 (13,14). The active p20 ICE product was detected at low levels at baseline in RAW264.7 cells, but its levels rapidly increased following treatment with anthrax LT (15 minutes). Bioactive p20 ICE was detected in J774A.1 cells within 2 hours of anthrax LT treatment. ICE activation was observed in both cell lines immediately prior to the onset of cell toxicity, which occurred approximately 2-4 hours following treatment.

EXAMPLE 3

ICE-Specific Inhibitor Blocks Production of IL-1β and IL-18

This example describes methods used to demonstrate that ICE activity led to extracellular release of activated IL-1β and IL-18 in anthrax LT-treated macrophages, by using a specific inhibitor of activated ICE, Z-WEHD-FMK.

Cultures of RAW264.7 cells were pre-treated with or without increasing concentrations of caspase-1 inhibitor, Z-WEHD-FMK (R&D Systems, Minneapolis, Minn.). Z-WEHD-FMK was reconstituted in DMSO to make a stock solution of 20 mM. Following 30 minutes of pre-treatment, cultures were treated with or without a fixed concentration of anthrax LT as indicated (see Example 1 for methods). ELISA was used to measure the extracellular cytokine concentrations of IL-1β and IL-18 as described in Example 1.

Figure 3B:
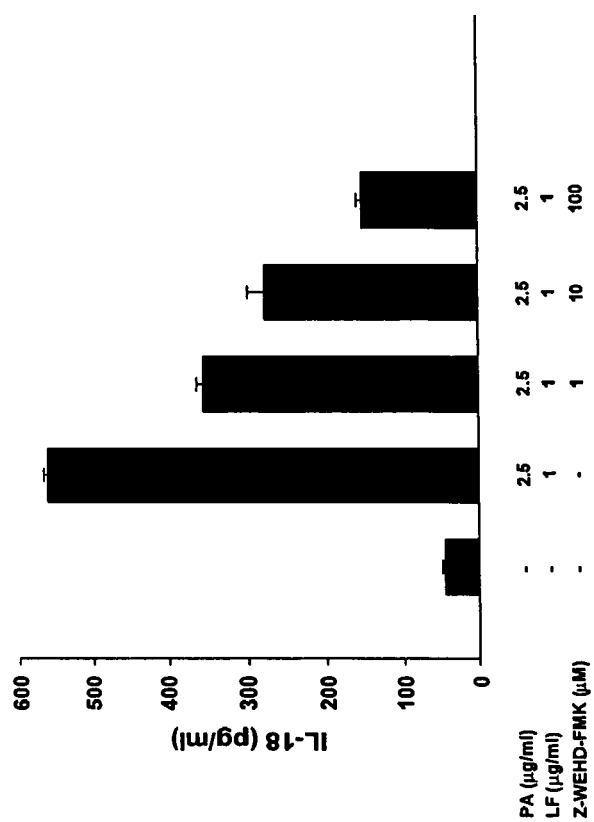
FIGS. 3A and 3B are bar graphs showing the dose-dependent inhibition of IL-1β (A) and IL-18 (B) induction by the ICE inhibitor Z-WEHD-FMK. Values represent the average extracellular cytokine concentrations of IL-1β (A) and IL-18 (B) measured by ELISA in duplicate. Bars indicate intra-assay standard deviation.
Figure 3A:
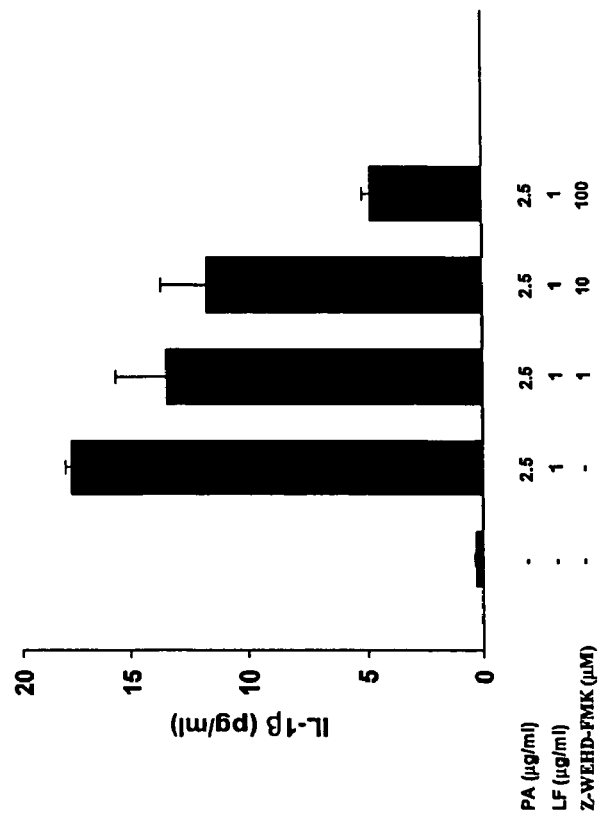

Z-WEHD-FMK had no observable effect on cell viability. As shown in FIGS. 3A and 3B, anthrax LT treatment alone led to induction of IL-1β and IL-18 in RAW264.7 cells following 24 hours of treatment. Administration of Z-WEHD-FMK prior to anthrax LT treatment blocked induction of IL-1β and IL-18. The inhibition of cytokine induction was dose-dependent. At a dose of 100 μM, Z-WEHD-FMK blocked nearly 70% of the production of IL-1β (FIG. 3A) and IL-18 (FIG. 3B) induced by 1 μg/ml anthrax LF, a dose that was 10-fold greater than the minimum anthrax LT dose required to induce plateau levels of IL-1β and IL-18 production.

EXAMPLE 4

Anthrax LT Increases Plasma Levels of IL-1β and IL-18 In Vivo

This example describes methods used to demonstrate that anthrax LT also increases the amount of activated IL-1β and IL-18 in vivo.

BALB/c and C57BL/6 4-8 week old mice (Jackson Laboratories, Bar Harbor, Me.) were treated with anthrax LT, and plasma levels of IL-1β and IL-18 determined using the following methods. Animals received intraperitoneally (i.p.) administered of LF (20 μg) and/or PA (50 μg) or vehicle control (PBS). Blood was obtained from animals sacrificed at the indicated time points, and plasma cytokine levels were determined by ELISA (R&D Systems) as described in Example 1.

Figure 4A:
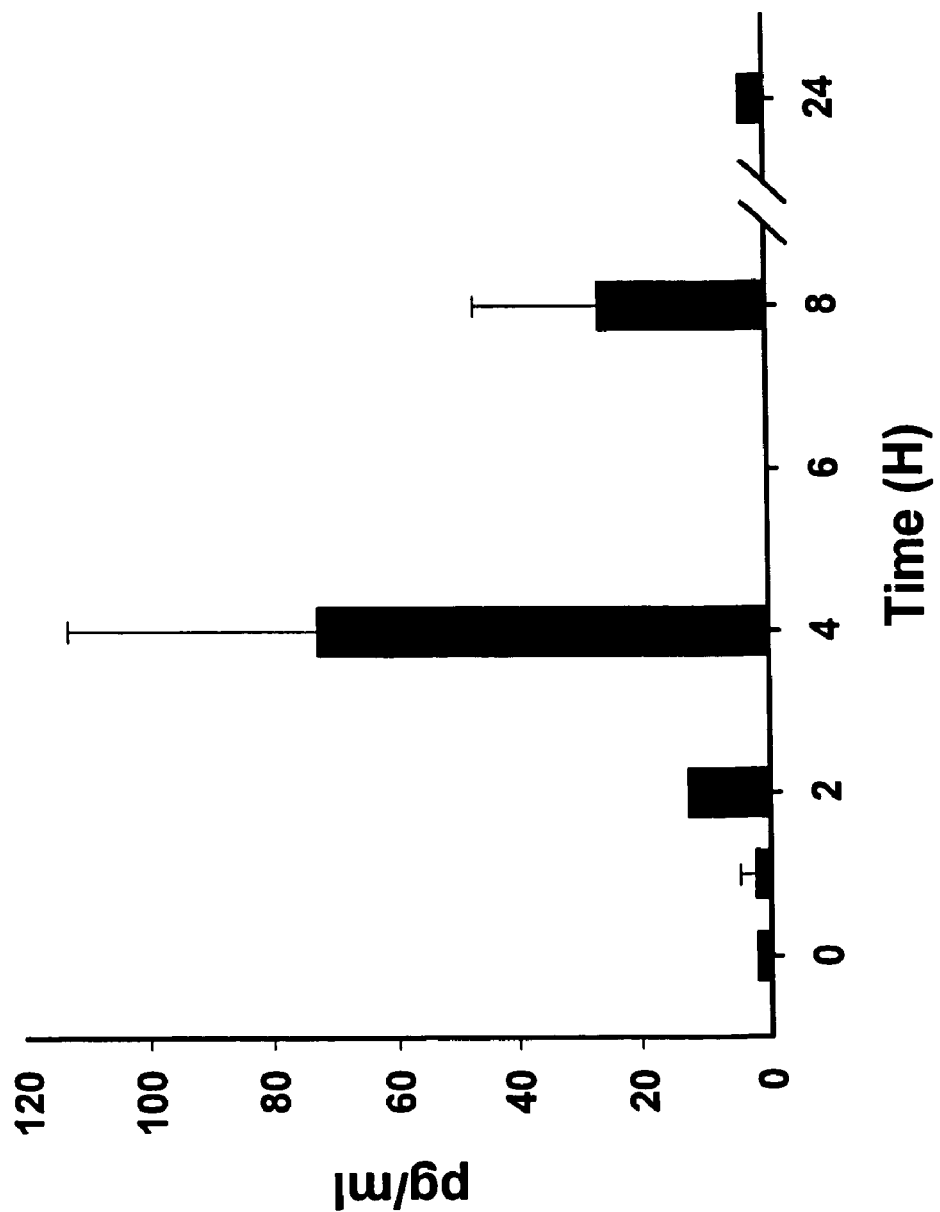
FIGS. 4A and 4B showing the increase in pro-inflammatory cytokines IL-1β (A) and IL-18 (B) in the sera of anthrax LT-treated mice. Data shown represents the values from single animals or duplicate animals (with range of variability indicated).
Figure 4B:
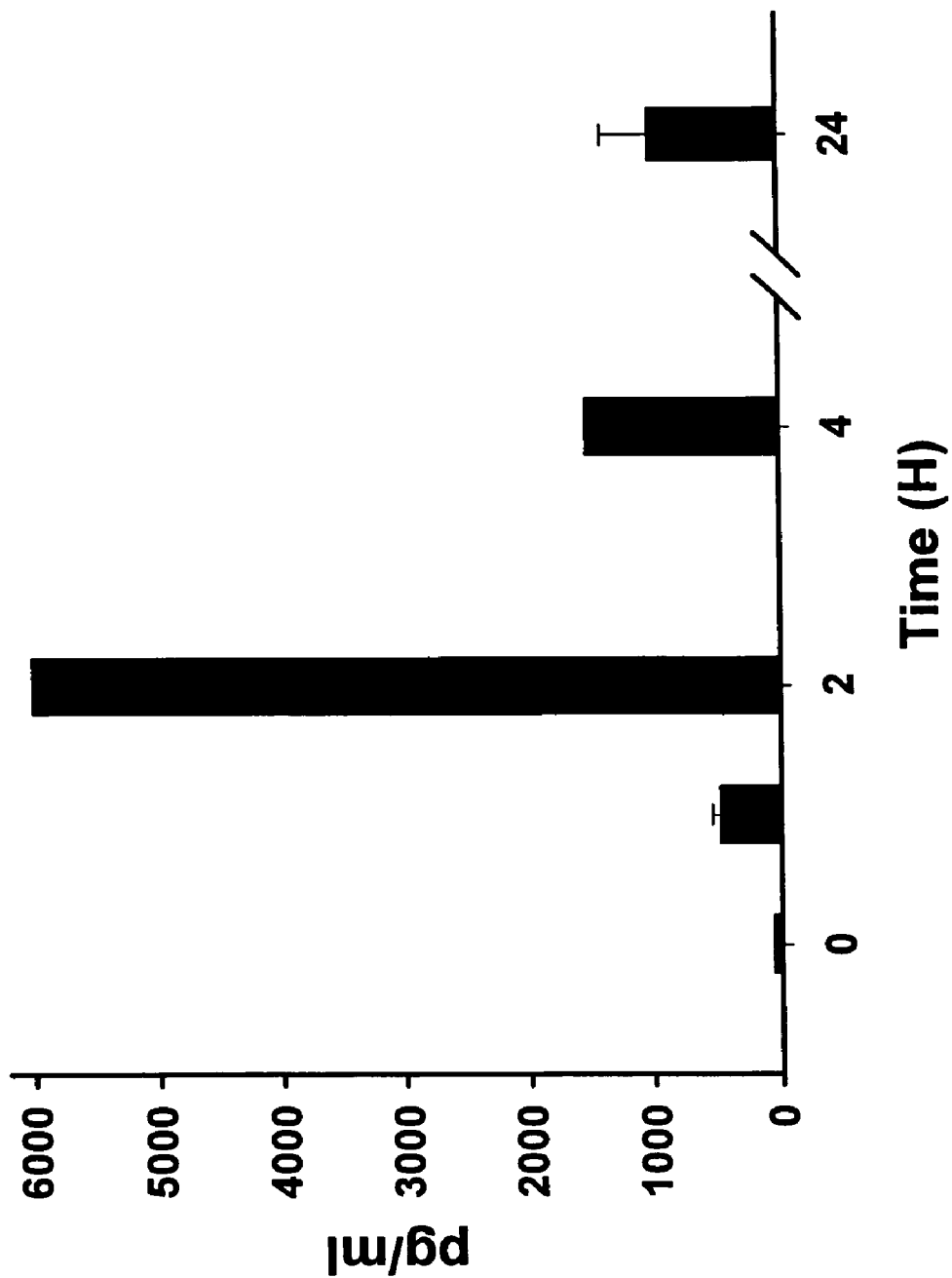
Figure 4C:
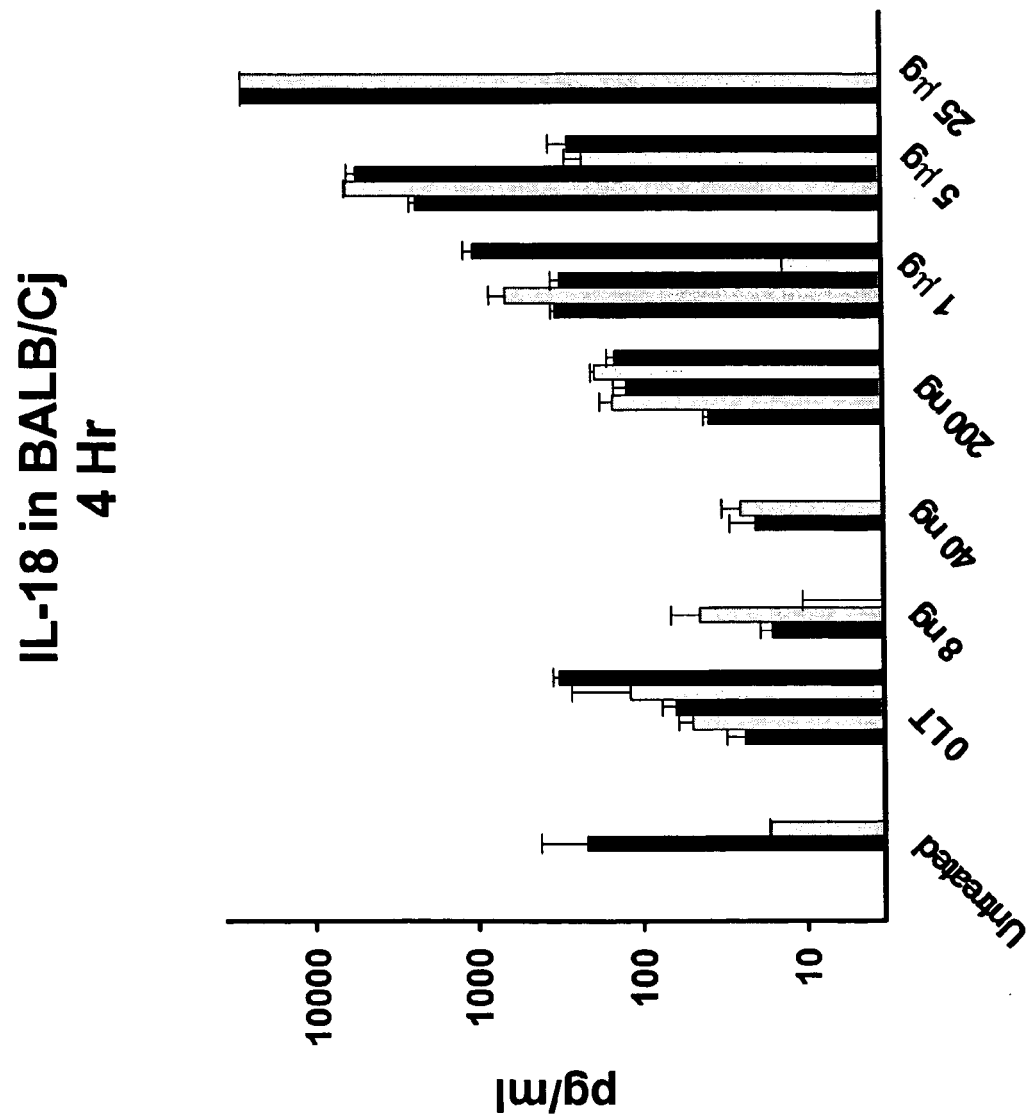
FIG. 4C is a bar graph showing the IL-18 levels in the sera of BALB/c mice treated with increasing doses of LF (as shown) and PA (fixed ratio, 2.5× the LF dose). Shown are the results from individual animals with error bars representing intra-assay standard deviation of ELISA replicates.

As shown in FIGS. 4A and 4B, plasma levels of activated IL-1β and IL-18 in BALB/c mice increased rapidly following anthrax LT treatment. Four hours following anthrax LT treatment, plasma IL-18 levels increased to more than 10 ng/mL in mice treated with 25 μg of LF in the presence of non-limiting doses of PA (FIG. 4C). Moreover, an increase in IL-18 levels was detected at an LF dose as low as 1 μg, which is well below the lethal dose (FIG. 4C).

Figure 4D:
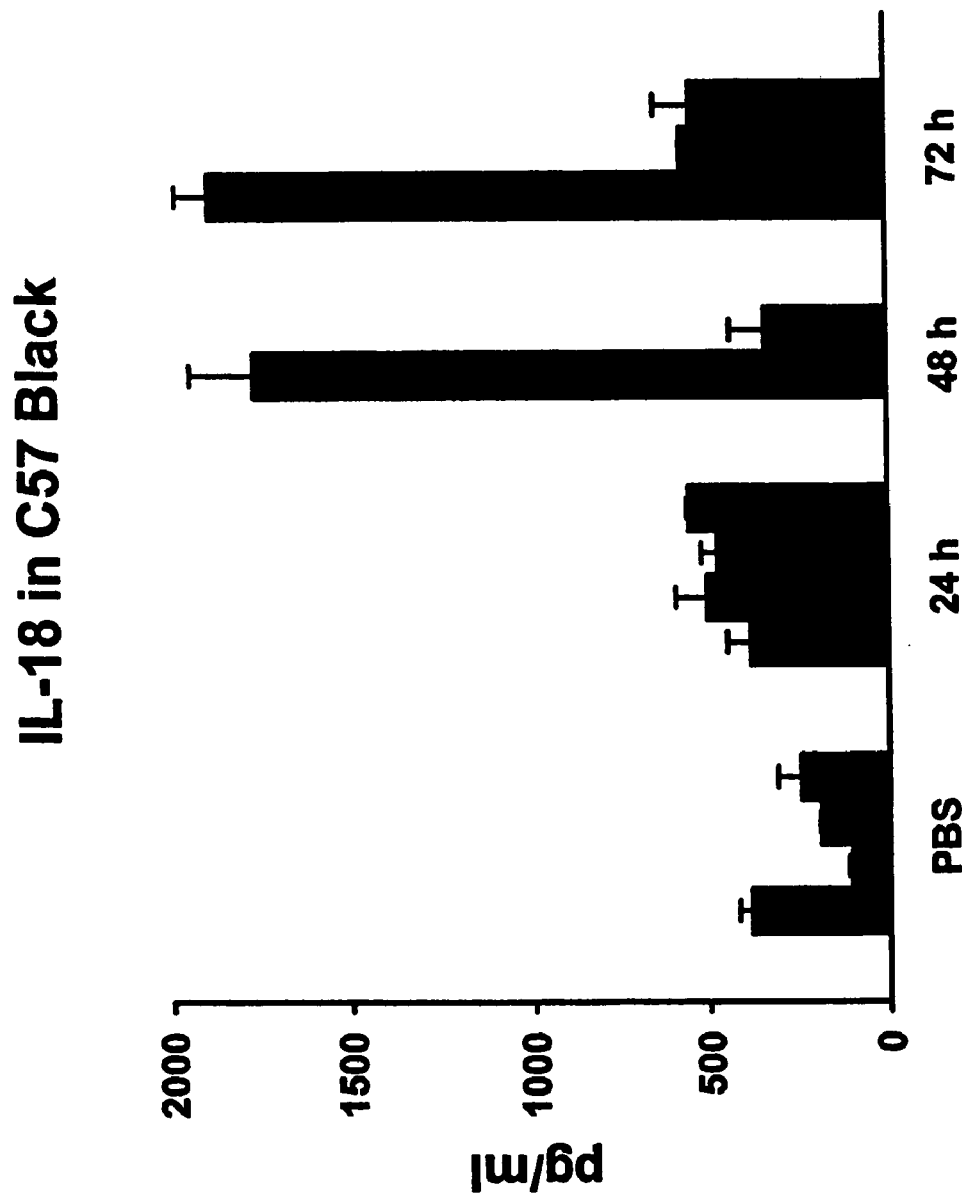
FIG. 4D is a bar graph showing the IL-18 levels in the sera of C57BL/6 mice were treated with 100 µg of LF and 250 µg of PA. Plasma IL-18 levels from individual animals are shown with error bars representing intra-assay standard deviation of ELISA replicates.

The regulation of IL-18 in C57BL/6 mice, which have been reported by others to be relatively resistant to anthrax LT, was also determined. Although another group reported no effect of anthrax LT on serum IL-18 levels in C57BL mice (Moayeri et al. *J. Clin. Invest.* 112:670-82, 2003), FIG. 4D demonstrates that IL-18 induction was observed in a subset of C57BL mice at late time points (2-3 days post anthrax LT treatment). Therefore, activation of the ICE/Caspase-1 pathway is not restricted to the BALB/c strain, as are the currently available anthrax LT biomarkers (such as proliferation and cell lysis).

The results presented in Examples 1-4 demonstrate that the use of bioassays based on ICE, IL-1β, or IL-18 have broader relevance to disease pathology than existing strain- and species-specific assays. The production of ICE-dependent proinflammatory cytokines may represent a more suitable biomarker for anthrax LT activity than its action to cause cell death.

The finding that anthrax LT activates ICE (Examples 2 and 3) provides an explanation for the variability in published reports. ICE plays roles in two potentially competing pathways, participating in both pro-apoptotic and pro-inflammatory pathways. Thus, species-specific, cell-specific, and activation state-specific variability to anthrax LT may be based on the relative strength of these signaling pathways.

EXAMPLE 5

In Vitro Bioassays

This example describes exemplary in vitro assays that can be used to determine the efficacy of a test agent, for example its ability to treat a subject having an anthrax infection or protect a subject from infection in the future (prophylaxis). Such assays can therefore be used to identify therapeutic agents that can decrease the pathogenicity of anthrax. Although particular examples are provided using mouse macrophages and detecting ICE activity, one skilled in the art will appreciate that other in vitro assays can be used. For example, different cell lines and other assays for determining ICE activity (such as measuring an amount of ICE or ICE-dependent cytokine activated, or by measuring the biological activity of ICE, for example by determining the activity of an ICE-dependent cytokine) can be used.

In particular examples, the method includes incubating a cell expression ICE with one or more test agents. In some examples, the cell is also infected with anthrax. Infecting the cell with anthrax can include infection with *B. anthracis* spores or with anthrax toxin (for example anthrax LT). Subsequently, ICE activity is determined. For example, ICE activity can be determined by measuring functional activity of ICE or an ICE-dependent cytokine (such as IL-1β or IL-18) or by determining an amount of activated ICE or activated ICE-dependent cytokine (such as activated IL-1β or activated IL-18) present. In particular examples, the method further includes comparing the observed ICE activity to a control.

In a particular example, the mouse macrophage cell line J744A.1 or RAW264.7 is used. Cells in culture are contacted with a test agent, for example before, during or following infection with anthrax. In one example, the cells are infected with at least 104 *B. anthracis* spores of the 7702 strain for at least 30 minutes. In another example, the cells are infected with at least 0.1 μg/ml of PA and at least 0.1 μg/ml of LF (for example at a ratio of at least 1:1 of PA:LF) for at least 10 minutes. In a particular example, the test agent is an antibody that specifically binds to anthrax LT.

In one example, ICE activity is determined by measuring an amount of ICE-dependent cytokine activated (such as an amount of IL-1β protein and IL-18 protein secreted into the cell culture supernatant) using the ELISA assay described in Example 1, for example at least 30 minutes following infection, such as at least 1 hour following infection. In addition, ICE activity can be determined by measuring an amount of ICE intracellular protein using Western blotting as described in Example 2. Agents that decrease ICE activity, for example by decreasing an amount or function of activated ICE or ICE-dependent cytokine (such as IL-1 or IL-18), such as a decrease of at least 10%, at least 20%, at least 50%, or even at least 95%, can be useful, for example, in treating an anthrax infection (for example reducing one or more symptoms of systemic shock) or decreasing infection by anthrax.

In particular examples, ICE activity is compared to a baseline, such as the activity present prior to addition of the test agent (or in the absence of the test agent). For example, the activity or amount of activated ICE or ICE-dependent cytokine (such as IL-1β or IL-18) can be compared to the activity or amount present prior to addition of the test agent. In another example, ICE activity is compared to a control sample, such as a sample not incubated with the test agent (positive control), or a sample not incubated with the test agent and not infected with anthrax (negative control). Test agents that decrease ICE activity (such as a decrease the function or amount of activated ICE or ICE-dependent cytokine such as IL-1β or IL-18) relative to the baseline or the positive control, such as a decrease of at least 20%, can be useful, for example, in treating an anthrax infection or decreasing infection by anthrax. Similarly, test agents that have a similar amount of ICE activity (such as similar function or amount of activated ICE or ICE-dependent cytokine such as IL-1β or IL-18) relative to the negative control, such as a change of no more than 10%, can be useful, for example, in treating an anthrax infection or decreasing infection by anthrax.

Agents identified to be therapeutically useful in vitro can be selected and analyzed for their ability to have similar therapeutic effects in vivo (for example using the methods described in Example 6).

EXAMPLE 6

In Vivo Bioassays

This example describes in vivo methods that can be used to screen a potential anthrax therapeutic agent for its ability to treat a subject infected with *B. anthracis* or protect a subject from infection in the future (prophylaxis). Alternatively, the methods can be used to demonstrate in vivo activity of agents originally identified using in vitro assays (such as those described in Example 5). One skilled in the art will appreciate that other in vivo assays can be used. For example, different subjects can be used, and other assays for determining ICE activity can be used. In addition, the methods described herein can be used to infect a subject with anthrax, and subsequently cells isolated from the subject are cultured and test agents analyzed in vitro, for example using the in vitro methods described in Example 5.

The disclosed in vivo assays are similar to the disclosed in vitro assays, wherein contacting the cell with the test agent in vivo includes administering the test agent to the subject. In examples where the cell is infected with anthrax, the method includes infecting the subject with anthrax (such as with *B. anthracis* spores or anthrax LT). For example, the in vivo method can include infecting an animal with anthrax and administering one or more test agents (such as at least one test agent, at least two test agents, or at least three test agents) to the subject. The infection and administration of the one or more test agents can be simultaneous, or one subsequent to the other. Infecting the animal with anthrax can include administering *B. anthracis* spores (such as $10^4$-$10^8$ spores/ml having an MOI of about 1:1) or anthrax toxin (such as LT, for example at a ratio of at least 1:1 of PA:LF, such as at least 2:1 PA:LF) to the subject. Particular exemplary doses are provided below. Exemplary strains of *B. anthracis* spores that can be used, and exemplary anthrax toxins, are provided herein. Subsequently, the ICE activity in the subject is determined. For example, a biological sample can be obtained from the subject, such as a blood sample, and the ICE activity present in the sample determined.

In one example, ICE activity is determined by measuring an amount of ICE-dependent cytokine activated (such as an amount of IL-1β protein and IL-18 protein secreted into the serum or plasma of the subject) using the ELISA assay described in Example 1, for example at least 30 minutes following infection, such as at least 1 hour following infection. In addition, ICE activity can be determined by measuring an amount of ICE intracellular protein (for example, an amount of activated ICE present in a cell lysate prepared from a sample of the subject containing cells) using Western blotting as described in Example 2. Agents that decrease ICE activity, for example by decreasing the function or amount of activated ICE or ICE-dependent cytokine (such as IL-1β or IL-18), such as a decrease of at least 10%, at least 20%, at least 50%, or even at least 95%, can be useful, for example, in treating an anthrax infection (for example reducing one or more symptoms of systemic shock) or decreasing infection by anthrax.

In particular examples, ICE activity is compared to a baseline, such as the activity present prior to addition of the test agent (or in the absence of the test agent). For example, the activity or amount of activated ICE or ICE-dependent cytokine (such as IL-1β or IL-18) can be compared to an activity or amount present in the subject prior to addition of the test agent. In another example, ICE activity is compared to a control, such as a sample that includes ICE activity present in the absence of the test agent and in the presence of anthrax (*B.*

*anthracis* spores or anthrax LT), such as a sample from subject exposed to or infected with anthrax prior to receiving a therapeutic agent (positive control), or a sample that includes ICE activity present in the absence of the test agent and anthrax, such as a sample from a subject not infected with or exposed to anthrax (negative control). Test agents that decrease ICE activity (such as decrease the function or amount of activated ICE or ICE-dependent cytokine such as IL-1β or IL-18) relative to the baseline or the positive control, such as a decrease of at least 20%, can be useful, for example, in treating an anthrax infection or decreasing infection by anthrax. Similarly, test agents that have a similar an amount of ICE activity (such as similar function or amount of activated ICE or ICE-dependent cytokine such as IL-1β or IL-18) relative to the negative control, such as a change of no more than 10%, can be useful, for example, in treating an anthrax infection or decreasing infection by anthrax.

Agents identified to be therapeutically useful in vivo can be selected and analyzed for their ability to have similar therapeutic effects in a human subject, and to determine the therapeutically effective dose.

Exemplary Animals and Doses

Rhesus macaques (*Macaca mulatta*) are the most commonly used nonhuman primate model of human inhalation anthrax exposure. Methods infecting rhesus macaques with *B. anthracis* spores are known (for example see Fritz et al., *Lab. Invest.* 73:691-702, 1995). Briefly, *rhesus macaques* (such as those at 3-15 kg) are infected with virulent *B. anthracis* spores (such as spores of the Ames strain) via aerosol challenge as follows. The rhesus macaques are exposed in a head-only chamber to a spore aerosol generated by a three-jet Collison nebulizer. For each animal, the concentration of spores in the aerosol inhaled dose (expressed as $LD_{50}$) is determined by plating a sample from an all glass impinger onto trypic soy agar plates. One aerosol $LD_{50}$ in rhesus macaques is $5.5 \times 10^4$ spores. In particular examples, animals infected by aerosol can receive about 5-100 $LD_{50}$ of spores, such as 50-100 $LD_{50}$ of spores. The spores can be diluted in water. The animals can be anesthetized during the infection procedure. Before or after the aerosol challenge, the animal is administered one or more test agents (for example in combination with a pharmaceutically acceptable carrier). A separate group of control animals can be administered phosphate-buffered saline (PBS) as a negative control.

However, other nonhuman primates can also be used, such as *cynomolgus macaques* (*Macaca fascicularis*) (for example see Vasconcelos et al., Lab. Invest. 83:1201-9, 2003). Briefly, cynomolgus monkeys (such as those about 1.5 to 5 kg) can be exposed to aerosolized spores of *B. anthracis* (such as the Ames strain) in a head-only exposure chamber as described above. The animals can be anesthetized during the infection procedure. The $LD_{50}$ is 61,800 CFU for the Ames strain. In particular examples, each cynomolgus monkey is exposed to $10^4$-$10^7$ CFUs of *B. anthracis*.

Guinea pigs are yet another animal model of anthrax infection (for example see Fellows et al. *Vaccine* 19:3241-7, 2001 and Marcus et al. *Infect. Immun.* 72:3471-7, 2004). In one example, the guinea pig is a Hartley guinea pig (Charles River, Wilmington, Mass.), such as one that is about 200-400 g. Methods of infecting a guinea pig with anthrax are known. For example, parenteral administration can be used, for example by injecting spores intramuscularly or intradermally. In a particular example, guinea pigs are infected with an at least 40% lethal dose ($LD_{50}$), such as an at least 50% $LD_{50}$, at least 80% $LD_{50}$, or an at least 100% $LD_{50}$. In one example, 5,000 to 10,000 *B. anthracis* spores are administered (10,000 spores are 100 $LD_{50}$ Ames equivalents). In another example, animals are administered 2,000 spores of *B. anthracis* strain Vollum (ATCC 14578).

Another model of anthrax infection is the rabbit. Methods of infecting a rabbit with anthrax by inhalation or subcutaneous inoculation are known (for example see Zaucha et al. *Arch. Pathol. Lab. Med.* 122:982-92, 1998). For example, New Zealand white rabbits (*Oryctolagus cuniculus*) can be exposed to *B. anthracis* spores (for example via aerosol or subcutaneous inoculation). For subcutaneous administration, spores of the desired *B. anthracis* strain (such as the Ames strain) can be suspended in a sterile carrier (such as water or PBS) at the desired concentration (for example $10^2$ to $10^5$ CFU at 0.5 ml/dose). The spores are injected into the rabbit, for example in the dorsal interscapular region. For aerosol exposure, the methods described above can be used (for example at a dose of $10^4$ to $10^8$ CFU). In particular examples, rabbits are exposed using a nose-only chamber, instead of a head-only chamber.

Although the examples above describe administration of *B. anthracis* spores, anthrax toxin can also be administered to a subject. Lethal toxin (LT), the combination of LF and PA, is sufficient to induce many of the laboratory manifestations of anthrax disease in animal models. For example, Moayeri et al., (*J. Clin. Invest.* 112(5):670-82, 2003) describe administration of toxin to mice. Briefly, BALB/cJ or C57BL/6J mice, such as those 6-8 weeks old, are injected with toxin (such as 50 µg, 100 µg, or 250 µg of each toxin component, LF and PA). For example, in a mouse, volumes that can be used for injection, include, but are not limited to 1 ml intraperitoneally (i.p.) and 10-100 µl intravenously (i.v.).

Similarly, Maynard et al. (*Nat. Biotechnol.* 20:597-601, 2002) describe administration of toxin to Fisher 344 rats. Briefly, Fisher 344 rats (such as those about 200-300 g) are injected with toxin (such as 30-50 µg PA and 5-20 µg LF) in a 200 µl volume, for example via penile vein injection.

EXAMPLE 7

Methods of Diagnosing Anthrax Disease

Based on the observation that increased amounts of activated IL-1β and IL-18 are observed in plasma from mice infected with anthrax LF, this example provides methods of diagnosing an anthrax infection in a subject.

The method of diagnosis includes detecting ICE activity (for example as measured by levels of activated ICE or ICE-dependent cytokines, such as IL-1β and IL-18) in a sample from the subject, wherein an increase in ICE activity indicates that the subject has an anthrax infection or has been exposed to anthrax spores or LT. The subject can be one thought to be infected with *B. anthracis*, or a subject at risk for such infection (such as those that work with livestock, laboratory animals, or human subjects infected with *B. anthracis*).

Methods of obtaining biological samples are known in the art. Any biological sample that could contain ICE activity (such as those that could contain ICE, IL-1β or IL-18 nucleic acid molecules or proteins, such as active-forms of such proteins) can be used. Particular examples of biological samples, include, but are not limited to blood, serum, plasma, and tissue biopsies. In one example, plasma is obtained from the subject. Methods of obtaining such samples are known in the art.

Methods of determining ICE activity are disclosed herein. However, one skilled in the art will appreciate that other methods can be used. For example, ICE activity can be determined by measuring the intracellular or extracellular functional activity or amounts of ICE or an ICE-dependent cytokine. In a specific example, a serum or plasma sample is used to determine an amount of extracellular activated ICE-dependent cytokine present in the subject, such as an amount of activated IL-1β or IL-18. In anther example, a biological sample containing cells is lysed, and the intracellular amount of activated ICE determined.

In particular examples, the ICE activity in the subject is compared to a baseline or to a control. When comparing ICE activity present in the subject to a negative control (such as a sample that includes a reference amount of ICE activity expected when a subject is not infected with, or exposed to, anthrax), an increase in ICE activity compared to the control indicates that the subject is infected with anthrax. Examples of such increases include an increase of at least 20%, at least 50%, or even at least 95% relative to the negative control. When comparing ICE activity present in the subject to a positive control (such as a sample that includes a reference amount of ICE activity expected when a subject is infected with, or exposed to, anthrax), a decrease in ICE activity compared to the positive control indicates that the subject is not infected with anthrax. Examples of such decreases include a decrease of at least 20%, at least 50%, or even at least 95% relative to the positive control.

EXAMPLE 8

Methods of Treating Anthrax Disease

Based on the observation that increased production of activated IL-1β and IL-18 are observed in plasma from mice infected with anthrax LF, the present disclosure provides methods of treating an anthrax infection, by decreasing the ICE activity in the subject. Methods of treatment include methods that reduce one or more symptoms in the subject due to the infection, such as fever, systemic shock, inflammation, or blisters on the skin. However, a complete elimination of symptoms is not required. Treatment methods can also include reducing the presence of biologically active anthrax LT in a subject.

ICE activity can be decreased, for example by functionally impairing an ICE-dependent cytokine (such as IL-1β or IL-18) or reducing the amount of an ICE-dependent cytokine available to participate in the pathogenesis of an anthrax infection. Such amounts can be reduced for example, by interfering with the production of biologically active forms of ICE-dependent cytokines, or the functional activity of ICE or its ICE-dependent cytokines. Such interference is achieved in one example by interfering with cleavage of a precursor molecule, such as ICE.

In particular examples, the method includes administering to the subject a therapeutically effective amount of an agent that decreases the biological activity of an ICE-dependent cytokine such as IL-1β or IL-18. When the activity of an ICE-dependent cytokine is decreased, for example by prematurely downregulating protein or nucleic acid molecule levels, a reduction in one or more symptoms associated with anthrax infection is achieved. For example, antisense oligonucleotides, ribozymes, microRNAs, siRNA, and triple helix molecules that recognize a nucleic acid that encodes an ICE-dependent cytokine (such as IL-1β or IL-18), as well as a nucleic acid that encodes a precursor molecule, such as ICE, can therefore be used to disrupt cellular expression of ICE or ICE-dependent cytokine.

Nucleic acid molecules that decrease expression of ICE and ICE-dependent cytokines are known. For example, ICE siRNA expression vectors are available from IMGENEX (San Diego, Calif.). IL-18 antisense sequences are described in Bhakoo et al. (*Mol Immunol.* 41:1217-24, 2004), Zhang et al. (*Chin. Med J.* (*Engl*). 116:218-21, 2003), and Wirtz et al. (*Immunol.* 168:411-20, 2002). IL-1β antisense sequences are described in Zhao et al. (*J. Neurosci.* 24:2226-35, 2004) and Heal et al., (*Mol. Immunol.* 36:1141-8, 1999). In particular examples, antisense, ribozyme, triple helix, microRNAs, and siRNA molecules are administered at a concentration of 1-10 mg nucleic acid molecule/kg of subject, such as 1-5 mg/kg, or 3-7 mg/kg.

Similarly, other agents, such as an agent that specifically recognizes and interacts with (such as binds to) pro- or active-forms of ICE protein or an ICE-dependent cytokine (such as IL-1β or IL-18), thereby decreasing the biological activity of such proteins, can also be used to treat an infection. In one particular example, such an agent is an antibody, such as a monoclonal, polyclonal, or humanized antibody.

Other exemplary agents are those identified using the methods described in the Examples above. These agents, such as antibodies, peptides, nucleic acid molecules, organic or inorganic compounds, can be administered to a subject in a therapeutically effective amount. After the agent has produced an effect (for example at least one symptom associated with anthrax infection decreases), for example after 24-48 hours, the subject can be monitored for symptoms associated with the infection.

Therapeutic agents can be administered alone, or with a pharmaceutically acceptable carrier. Furthermore, the pharmaceutical compositions or methods of treatment can be administered in combination with (such as before, during, or following) other therapeutic treatments, such as other anti-anthrax agents. In one example, the subject is a mammal, such as a mouse, non-human primate, or human.

EXAMPLE 9

Pharmaceutical Compositions and Modes of Administration

Methods for administering *B. anthracis* spores by any method known in the art, such as aerosol inhalation, injection (such as subcutaneous, intramuscular, intravenous, or intraperitoneal).

Similarly, methods of administering one or more test agents or a therapeutic agent are known. Methods of introduction include, but are not limited to, topical, intradermal, intramuscular, intraperitoneal, intravenous, subcutaneous, intranasal, and oral routes. In an example in which a nucleic acid molecule is the test agent (or therapeutic molecule), such as an antisense, ribozyme, triple helix, miR, or siRNA molecule, any method known in the art can be used. Particular examples include delivering the nucleic acid molecule intracellularly (for example by receptor-mediated mechanisms), by an expression vector administered so that it becomes intracellular (for example by use of a retroviral vector, see U.S. Pat. No. 4,980,286), by injection of the nucleic acid molecule to a cell, by use of microparticle bombardment (such as a gene gun; Biolistic, Dupont), coating the nucleic acid molecule with lipids or cell-surface receptors or transfecting agents, or by administering it in linkage to a homeobox-like peptide known to enter the nucleus (for example Joliot et al., *Proc. Natl. Acad. Sci. USA* 1991, 88:1864-8). The present disclosure includes all forms of nucleic acid molecule delivery, including synthetic oligos, naked DNA, plasmid and viral, integrated into the genome or not.

The *B. anthracis* spores, anthrax toxin, or test agent can be administered to an animal in the presence of a pharmaceutically acceptable carrier. *Remington's Pharmaceutical Sciences*, by Martin, Mack Publishing Co., Easton, Pa., 15th Edition (1975), describes compositions and formulations suitable for pharmaceutical delivery of the agents herein disclosed. In general, the nature of the carrier will depend on the mode of administration employed. For instance, parenteral formulations usually include injectable fluids that include pharmaceutically and physiologically acceptable fluids such as water, physiological saline, balanced salt solutions, aqueous dextrose, sesame oil, glycerol, ethanol, combinations thereof, or the like, as a vehicle. The carrier and composition can be sterile, and the formulation suits the mode of administration. In addition to biologically-neutral carriers, pharmaceutical compositions to be administered can contain minor amounts of non-toxic auxiliary substances, such as wetting or emulsifying agents, preservatives, and pH buffering agents and the like, for example sodium acetate or sorbitan monolaurate.

The composition can be a liquid solution, suspension, emulsion, tablet, pill, capsule, sustained release formulation, or powder. For solid compositions (for example powder, pill, tablet, or capsule forms), conventional non-toxic solid carriers can include, for example, pharmaceutical grades of mannitol, lactose, starch, sodium saccharine, cellulose, magnesium carbonate, or magnesium stearate. The composition can be formulated as a suppository, with traditional binders and carriers such as triglycerides.

The amount of therapeutic agent effective in treating or preventing infection by anthrax can depend on the nature of the anthrax and its associated disorder or condition, and can be determined by standard clinical techniques. In addition, in vitro and in vivo assays can be employed to identify optimal dosage ranges, such as the assays described in Examples 6 and 7. For example, effective doses can be extrapolated from dose-response curves derived from in vitro or animal model test systems. The precise dose to be employed in the formulation will also depend on the route of administration, and the seriousness of the disease or disorder, and should be decided according to the judgment of the practitioner and each subject's circumstances.

In view of the many possible embodiments to which the principles of the disclosed invention may be applied, it should be recognized that the illustrated embodiments are only preferred examples of the invention and should not be taken as limiting the scope of the invention. Rather, the scope of the invention is defined by the following claims. We therefore claim as our invention all that comes within the scope and spirit of these claims.

We claim:

1. A method of identifying an agent that decreases anthrax-induced activation of caspase-1/IL-1 converting enzyme (ICE), comprising:
    contacting a test agent with a J774A.1 cell expressing ICE, wherein the cell expressing ICE is a cell infected with *Bacillus anthracis* spore(s) or exposed to an anthrax toxin that induces activation of ICE; and
    determining whether ICE activity is decreased in the cell, wherein determining whether ICE activity is decreased comprises comparing the ICE activity to a baseline or a control, wherein a decrease in ICE activity in the cell compared to the baseline or control indicates the test agent decreases anthrax-induced activation of ICE.

2. The method of claim 1, wherein determining whether ICE activity is decreased comprises determining an amount of activated IL-1β or activated IL-18 produced by the cell.

3. The method of claim 1, wherein the anthrax toxin comprises anthrax lethal toxin (LT).

4. The method of claim 1, wherein the control comprises a second cell infected with *Bacillus anthracis* spore(s) or exposed to an anthrax toxin and expressing ICE but not contacted with the test agent, wherein a decrease in ICE activity in the cell compared to the second cell indicates the test agent decreases anthrax-induced activation of ICE.

5. The method of claim 1, wherein the test agent comprises an antibody that recognizes anthrax LT.

6. The method of claim 2, wherein determining whether ICE activity is decreased comprises determining an amount of activated IL-1β or activated IL-18 secreted by the cell.

* * * * *